(12) United States Patent
Shalev

(10) Patent No.: US 9,486,341 B2
(45) Date of Patent: Nov. 8, 2016

(54) REDUCED-STRAIN EXTRA-VASCULAR RING FOR TREATING AORTIC ANEURYSM

(75) Inventor: Alon Shalev, Ra'anana (IL)

(73) Assignee: ENDOSPAN LTD., Herzilyia Pituach (IL)

(*) Notice: Subject to any disclaimer, the term of this patent is extended or adjusted under 35 U.S.C. 154(b) by 378 days.

(21) Appl. No.: 14/001,641

(22) PCT Filed: Mar. 1, 2012

(86) PCT No.: PCT/IL2012/000095
§ 371 (c)(1),
(2), (4) Date: Nov. 5, 2013

(87) PCT Pub. No.: WO2012/117395
PCT Pub. Date: Sep. 7, 2012

(65) Prior Publication Data
US 2014/0052236 A1  Feb. 20, 2014

Related U.S. Application Data

(60) Provisional application No. 61/448,199, filed on Mar. 2, 2011.

(51) Int. Cl.
*A61F 2/93* (2013.01)
*A61F 2/07* (2013.01)
(Continued)

(52) U.S. Cl.
CPC . *A61F 2/93* (2013.01); *A61F 2/07* (2013.01); *A61B 17/12013* (2013.01); *A61F 2/89* (2013.01);
(Continued)

(58) Field of Classification Search
CPC .......... A61F 2/92; A61F 2/93; A61F 2/2409; A61F 2/07; A61B 17/12013
See application file for complete search history.

(56) References Cited

U.S. PATENT DOCUMENTS

| 4,355,426 A | 10/1982 | MacGregor |
| 4,505,767 A | 3/1985 | Quin |

(Continued)

FOREIGN PATENT DOCUMENTS

| CA | 2 497 704 | 3/2004 |
| EP | 1 177 780 | 2/2002 |

(Continued)

OTHER PUBLICATIONS

Communication dated Nov. 10, 2014, issued by the European Patent Office in counterpart Application No. 12752054.2.
(Continued)

*Primary Examiner* — Thomas McEvoy
(74) *Attorney, Agent, or Firm* — Sughrue Mion, PLLC

(57) ABSTRACT

Apparatus (10) is provided that includes an extra-vascular ring (12) and an endo vascular stent-graft (14). The ring (12) comprises a structural member (30), which is configured to assume an elongate hollow shape (32), which has first and second longitudinal ends (40, 42), and is suitable for placement at least partially around an aorta (20) so as to provide a generally cylindrical landing zone. The endovascular stent-graft (14) is suitable for endovascular placement inside the aorta (20) such that a portion of the stent-graft (14) is positioned against an internal wall of the aorta (20) at the landing zone provided by the structural member (30). If the structural member (30) is unrolled to a planar shape (82), one side (90) of the planar shape (82) is defined by the first longitudinal end (40), and at least the first longitudinal end (40) has a profile that defines a series of curved portions and has no singularities or discontinuities, which profile extends along at least 50% of the first longitudinal end (40).

21 Claims, 10 Drawing Sheets

(51) Int. Cl.
*A61B 17/12* (2006.01)
*A61F 2/89* (2013.01)

(52) U.S. Cl.
CPC .. *A61F 2220/005* (2013.01); *A61F 2220/0025* (2013.01); *A61F 2220/0041* (2013.01); *A61F 2220/0066* (2013.01); *A61F 2220/0075* (2013.01); *A61F 2220/0083* (2013.01); *A61F 2230/0054* (2013.01)

(56) References Cited

U.S. PATENT DOCUMENTS

| | | |
|---|---|---|
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,816,339 A | 3/1989 | Tu et al. |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,234,448 A | 8/1993 | Wholey |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,591,229 A | 1/1997 | Parodi |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,774 A | 5/1998 | Pinchuk |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,827,321 A | 10/1998 | Roubin |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,976,178 A | 11/1999 | Goldsteen et al. |
| 5,980,552 A | 11/1999 | Pinchasik |
| 6,015,431 A | 1/2000 | Thornton et al. |
| 6,016,810 A | 1/2000 | Ravenscroft |
| 6,033,435 A | 3/2000 | Penn et al. |
| 6,036,725 A | 3/2000 | Avellanet |
| 6,059,824 A | 5/2000 | Taheri |
| 6,077,298 A | 6/2000 | Tu et al. |
| 6,099,497 A | 8/2000 | Adams et al. |
| 6,117,145 A | 9/2000 | Wood et al. |
| 6,152,956 A | 11/2000 | Pierce |
| 6,156,064 A | 12/2000 | Chouinard |
| 6,168,615 B1 | 1/2001 | Ken et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,296,661 B1 | 10/2001 | Davila et al. |
| 6,312,458 B1 | 11/2001 | Golds |
| 6,325,823 B1 | 12/2001 | Horzewski et al. |
| 6,344,056 B1 | 2/2002 | Dehdashtian |
| 6,406,420 B1 | 6/2002 | McCarthy |
| 6,428,565 B1 | 8/2002 | Wisselink |
| 6,451,048 B1 | 9/2002 | Berg et al. |
| 6,506,211 B1 | 1/2003 | Skubitz et al. |
| 6,565,597 B1 | 5/2003 | Fearnot et al. |
| 6,613,078 B1 | 9/2003 | Barone |
| 6,635,083 B1 | 10/2003 | Cheng et al. |
| 6,648,901 B2 | 11/2003 | Fleischman et al. |
| 6,648,911 B1 | 11/2003 | Sirhan |
| 6,652,567 B1 | 11/2003 | Deaton |
| 6,656,214 B1 | 12/2003 | Fogarty et al. |
| 6,692,520 B1 | 2/2004 | Gambale et al. |
| 6,695,833 B1 | 2/2004 | Frantzen |
| 6,730,117 B1 | 5/2004 | Tseng et al. |
| 6,743,195 B2 | 6/2004 | Zucker |
| 6,748,953 B2 | 6/2004 | Sherry et al. |
| 6,752,826 B2 | 6/2004 | Holloway |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,144,421 B2 | 12/2006 | Carpenter et al. |
| 7,201,772 B2 | 4/2007 | Schwammenthal et al. |
| 7,223,266 B2 | 5/2007 | Lindenbaum et al. |
| 7,261,733 B1 | 8/2007 | Brown et al. |
| 7,270,675 B2 | 9/2007 | Chun et al. |
| 7,279,003 B2 | 10/2007 | Berra et al. |
| 7,294,147 B2 | 11/2007 | Hartley |
| 7,306,623 B2 | 12/2007 | Watson |
| 7,341,598 B2 | 3/2008 | Davidson et al. |
| 7,399,313 B2 | 7/2008 | Brown et al. |
| 7,407,509 B2 | 8/2008 | Greenberg et al. |
| 7,429,269 B2 | 9/2008 | Schwammenthal et al. |
| 7,442,204 B2 | 10/2008 | Schwammenthal et al. |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,616,997 B2 | 11/2009 | Kieval et al. |
| 7,637,939 B2 | 12/2009 | Tischler |
| 7,662,161 B2 | 2/2010 | Briganti et al. |
| 7,662,168 B2 | 2/2010 | McGuckin, Jr. et al. |
| 7,678,141 B2 | 3/2010 | Greenan et al. |
| 7,708,704 B2 | 5/2010 | Mitelberg |
| 7,722,626 B2 | 5/2010 | Middleman et al. |
| 7,731,732 B2 | 6/2010 | Ken |
| 7,803,178 B2 | 9/2010 | Whirley et al. |
| 7,815,673 B2 | 10/2010 | Bloom et al. |
| 7,887,575 B2 | 2/2011 | Kujawski |
| 7,959,662 B2 | 6/2011 | Erbel et al. |

(56) References Cited

U.S. PATENT DOCUMENTS

| | | |
|---|---|---|
| 8,021,418 B2 | 9/2011 | Gerberding et al. |
| 8,052,741 B2 | 11/2011 | Bruszewski et al. |
| 8,066,755 B2 | 11/2011 | Zacharias et al. |
| 8,080,026 B2 | 12/2011 | Konstantino et al. |
| 8,080,053 B2 | 12/2011 | Satasiya et al. |
| 8,157,810 B2 | 4/2012 | Case et al. |
| 8,172,892 B2 | 5/2012 | Chuter et al. |
| 8,251,963 B2 | 8/2012 | Chin et al. |
| 8,353,898 B2 | 1/2013 | Lutze et al. |
| 8,486,131 B2 | 7/2013 | Shalev |
| 2001/0004705 A1 | 6/2001 | Killion et al. |
| 2001/0010006 A1 | 7/2001 | Bachinski et al. |
| 2001/0014823 A1 | 8/2001 | Ressemann et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0053930 A1 | 12/2001 | Kugler et al. |
| 2002/0040236 A1 | 4/2002 | Lau et al. |
| 2002/0099438 A1 | 7/2002 | Fursty |
| 2002/0099441 A1 | 7/2002 | Dehdashtian |
| 2002/0107564 A1 | 8/2002 | Cox et al. |
| 2002/0123791 A1 | 9/2002 | Harrison |
| 2002/0156495 A1 | 10/2002 | Brenneman et al. |
| 2003/0040791 A1 | 2/2003 | Oktay |
| 2003/0057156 A1 | 3/2003 | Peterson et al. |
| 2003/0068296 A1 | 4/2003 | Ricci et al. |
| 2003/0093145 A1 | 5/2003 | Lawrence-Brown et al. |
| 2003/0114061 A1 | 6/2003 | Matsuda et al. |
| 2003/0125796 A1 | 7/2003 | Dong |
| 2003/0130720 A1 | 7/2003 | DePalma et al. |
| 2003/0139802 A1 | 7/2003 | Wulfman et al. |
| 2003/0144725 A1 | 7/2003 | Lombardi |
| 2003/0153968 A1 | 8/2003 | Geis et al. |
| 2003/0163187 A1 | 8/2003 | Weber |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0133266 A1 | 7/2004 | Clerc et al. |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215319 A1 | 10/2004 | Berra et al. |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0070995 A1 | 3/2005 | Zilla et al. |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0143802 A1 | 6/2005 | Soykan et al. |
| 2005/0149166 A1 | 7/2005 | Schaeffer et al. |
| 2005/0154448 A1 | 7/2005 | Cully et al. |
| 2005/0171598 A1 | 8/2005 | Schaeffer et al. |
| 2005/0177132 A1 | 8/2005 | Lentz et al. |
| 2005/0203606 A1 | 9/2005 | VanCamp |
| 2005/0216018 A1 | 9/2005 | Sennett et al. |
| 2005/0222649 A1 | 10/2005 | Capuano et al. |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0234542 A1 | 10/2005 | Melsheimer |
| 2005/0266042 A1 | 12/2005 | Tseng |
| 2005/0283188 A1 | 12/2005 | Loshakove et al. |
| 2006/0015170 A1 | 1/2006 | Jones et al. |
| 2006/0052799 A1 | 3/2006 | Middleman et al. |
| 2006/0069426 A1 | 3/2006 | Weinberger |
| 2006/0095104 A1 | 5/2006 | Magers et al. |
| 2006/0100684 A1 | 5/2006 | Elliott |
| 2006/0106406 A1 | 5/2006 | Weinberger |
| 2006/0149360 A1 | 7/2006 | Schwammenthal et al. |
| 2006/0155358 A1 | 7/2006 | LaDuca et al. |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0281966 A1* | 12/2006 | Peacock ............... A61B 17/12 600/37 |
| 2007/0021822 A1 | 1/2007 | Boatman |
| 2007/0043425 A1 | 2/2007 | Hartley et al. |
| 2007/0050011 A1 | 3/2007 | Klein |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0167898 A1 | 7/2007 | Peters et al. |
| 2007/0179598 A1 | 8/2007 | Duerig |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0239256 A1 | 10/2007 | Weber et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0033527 A1 | 2/2008 | Nunez et al. |
| 2008/0058918 A1 | 3/2008 | Watson |
| 2008/0064957 A1 | 3/2008 | Spence |
| 2008/0086193 A1 | 4/2008 | Thramann |
| 2008/0109066 A1 | 5/2008 | Quinn |
| 2008/0114445 A1 | 5/2008 | Melsheimer et al. |
| 2008/0147173 A1 | 6/2008 | McIff et al. |
| 2008/0167704 A1 | 7/2008 | Wright et al. |
| 2008/0176271 A1 | 7/2008 | Silver et al. |
| 2008/0195190 A1 | 8/2008 | Bland et al. |
| 2008/0195191 A1 | 8/2008 | Luo |
| 2008/0215134 A1 | 9/2008 | Lawrence-Brown |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030502 A1 | 1/2009 | Sun et al. |
| 2009/0048663 A1 | 2/2009 | Greenberg |
| 2009/0054967 A1 | 2/2009 | Das |
| 2009/0069881 A1 | 3/2009 | Chalekian et al. |
| 2009/0069882 A1 | 3/2009 | Venturelli |
| 2009/0082841 A1 | 3/2009 | Zacharias et al. |
| 2009/0099648 A1 | 4/2009 | Yu |
| 2009/0099649 A1 | 4/2009 | Chobotov et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |

(56) References Cited

U.S. PATENT DOCUMENTS

| | | |
|---|---|---|
| 2009/0149877 A1 | 6/2009 | Hanson et al. |
| 2009/0164001 A1 | 6/2009 | Biggs et al. |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev |
| 2010/0070019 A1 | 3/2010 | Shalev |
| 2010/0161026 A1 | 6/2010 | Brocker et al. |
| 2010/0211159 A1 | 8/2010 | Schmid et al. |
| 2010/0256725 A1 | 10/2010 | Rasmussen |
| 2010/0274345 A1 | 10/2010 | Rust |
| 2010/0292774 A1 | 11/2010 | Shalev |
| 2011/0022149 A1 | 1/2011 | Cox et al. |
| 2011/0093002 A1 | 4/2011 | Rucker et al. |
| 2011/0125251 A1 | 5/2011 | Cottone |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0257725 A1 | 10/2011 | Argentine et al. |
| 2011/0262684 A1 | 10/2011 | Wintsch et al. |
| 2011/0264184 A1 | 10/2011 | Heltai |
| 2012/0143317 A1 | 6/2012 | Cam et al. |
| 2012/0158038 A1 | 6/2012 | Leschinsky |
| 2012/0179236 A1 | 7/2012 | Benary |
| 2012/0323305 A1 | 12/2012 | Benary |
| 2013/0274866 A1 | 10/2013 | Cox et al. |
| 2014/0364930 A1 | 12/2014 | Strauss et al. |

FOREIGN PATENT DOCUMENTS

| | | |
|---|---|---|
| EP | 1 325 716 | 7/2003 |
| JP | 2002253682 | 9/2002 |
| WO | 98/06355 A1 | 2/1998 |
| WO | 9934748 | 7/1999 |
| WO | 03/099108 | 12/2003 |
| WO | 2004/017868 | 3/2004 |
| WO | 2005/002466 | 1/2005 |
| WO | 2005/034809 A1 | 4/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 2006/070372 | 7/2006 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010027704 A1 | 3/2010 |
| WO | 2010/045238 | 4/2010 |
| WO | 2010/062355 | 6/2010 |
| WO | 2010/088776 | 8/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |
| WO | 2012/049679 | 4/2012 |
| WO | 2012/104842 | 8/2012 |
| WO | 2012/111006 | 8/2012 |
| WO | 2012/117395 | 9/2012 |
| WO | 2012/176187 | 12/2012 |
| WO | 2013/005207 | 1/2013 |
| WO | 2013/030818 | 3/2013 |
| WO | 2013/030819 | 3/2013 |
| WO | 2013/065040 | 5/2013 |
| WO | 2013/084235 | 6/2013 |
| WO | 2013/171730 | 11/2013 |

OTHER PUBLICATIONS

Communication dated Aug. 15, 2014, issued by the United States Patent and Trademark Office in counterpart Application No. 13939798.

Communication dated Sep. 2, 2014, issued by the United States Patent and Trademark Office in counterpart Application No. 12447684.

Communication dated Jul. 30, 2015 from the U.S. Patent and Trademark Office in counterpart application No. 14/240600.

Communication dated Aug. 12, 2015 from the U.S. Patent and Trademark Office in counterpart application No. 13/513397.

Communication dated Sep. 23, 2015 from the U.S. Patent and Trademark Office in counterpart application No. 13/384075.

Communication dated Oct. 2, 2015 from the U.S. Patent and Trademark Office in counterpart application No. 13/577161.

Communication dated Oct. 27, 2015 from the European Patent Office in counterpart application No. 10835608.0.

An Office Action dated Apr. 28, 2014, which issued during the prosecution of U.S. Appl. No. 13/939,798.

An English translation of an Office Action dated Nov. 28, 2013 which issued during the prosecution of Chinese Patent Application No. 200880126889.0.

"E-vita® open plus" product brochure (JOTEC GmbH, Hechingen, Germany), 2010.

Fonseca A et al., "Intravascular ultrasound assessment of the novel AngioSculpt scoring balloon catheter for the treatment of complex coronary lesions," J Invasive Cardiol 20(1):21-7 (Jan. 2008).

Khlif H et al., "Contribution to the Improvement of Textile Vascular Prostheses Crimping," Trends in Applied Sciences Research 6(9):1019-1027 (2011).

An International Search Report dated Sep. 29, 2008, which issued during the prosecution of Applicant's PCT/IL08/000287.

A Written Opinion dated Sep. 29, 2008, which issued during the prosecution of Applicant's PCT/IL08/000287.

An International Search Report dated Feb. 4, 2011, which issued during the prosecution of Applicant's PCT/IB2010/052861.

A Written Opinion dated Feb. 4, 2011, which issued during the prosecution of Applicant's PCT/IB2010/052861.

An International Search Report dated Dec. 3, 2010, which issued during the prosecution of Applicant's PCT/IL2010/000564.

A Written Opinion dated Dec. 3, 2010, which issued during the prosecution of Applicant's PCT/IL2010/000564.

An International Search Report dated Nov. 5, 2010, which issued during the prosecution of Applicant's PCT/IL2010/000549.

A Written Opinion dated Nov. 5, 2010, which issued during the prosecution of Applicant's PCT/IL2010/000549.

An International Search Report dated Aug. 4, 2011, which issued during the prosecution of Applicant's PCT/IL2010/000999.

An International Search Report dated Mar. 10, 2011, which issued during the prosecution of Applicant's PCT/IL2010/000917.

(56) References Cited

OTHER PUBLICATIONS

An International Search Report dated Mar. 30, 2011, which issued during the prosecution of Applicant's PCT/IL2010/001018.
An International Search Report dated Apr. 18, 2011, which issued during the prosecution of Applicant's PCT/IL2010/001037.
An International Search Report dated May 23, 2011, which issued during the prosecution of Applicant's PCT/IL2010/001087.
An International Search Report dated Jun. 28, 2011, which issued during the prosecution of Applicant's PCT/IL2011/000135.
An International Search Report dated Jun. 30, 2009, which issued during the prosecution of Applicant's PCT/IL2008/001621.
A Written Opinion dated Jun. 30, 2009, which issued during the prosecution of Applicant's PCT/IL2008/001621.
An International Search Report dated Mar. 11, 2009, which issued during the prosecution of Applicant's PCT/IL2007/001312.
A Written Opinion dated Mar. 11, 2009, which issued during the prosecution of Applicant's PCT/IL2007/001312.
An English translation of an Office Action dated Aug. 25, 2011, which issued during the prosecution of Chinese Patent Application No. 200880014919.9.
An Office Action dated Nov. 12, 2010, which issued during the prosecution of U.S. Appl. No. 12/447,684.
An Office Action dated Apr. 27. 2011, which issued during the prosecution of U.S. Appl. No. 12/447,684.
An International Preliminary Report on Patentability dated Aug. 4, 2009, which issued during the prosecution of Applicant's PCT/IL2007/001312.
An English Abstract of JP2002-253682 published Sep. 10, 2002.
An International Search Report and a Written Opinion both dated Jul. 13, 2012, which issued during the prosecution of Applicant's PCT/IL2012/000083.
An International Search Report and a Written Opinion both dated Mar. 15. 2013, which issued during the prosecution of Applicant's PCT/IL2012/050424.
U.S. Appl. No. 61/448,199, filed Mar. 2, 2011.
U.S. Appl. No. 61/014,031, filed Dec. 15, 2007.
An Examiner Interview Summary Report dated Dec. 13, 2010, which issued during the prosecution of U.S. Appl. No. 12/447 684.
U.S. Appl. No. 60/863,373, filed Oct. 29, 2006.
An Office Action together with its English Translation dated Feb. 16, 2013 which issued during the prosecution of Chinese Patent Application No. 200880126889.0.
A Restriction Requirement dated Mar. 21, 2012, which issued during the prosecution of U.S. Appl. No. 12/808,037.
An Office Action dated Jun. 19, 2012, which issued during the prosecution of U.S. Appl. No. 12/808,037.
An Office Action dated Feb. 27, 2013, which issued during the prosecution of U.S. Appl. No. 12/808,037.
A Notice of Allowance dated May 22, 2013, which issued during the prosecution of U.S. Appl. No. 12/808,037.
An International Search Report and a Written Opinion both dated Jul. 17, 2012, which issued during the prosecution of Applicant's PCT/IL2012/000095.
An International Preliminary Report on Patentability dated Sep. 3, 2013, which issued during the prosecution of Applicant's PCT/IL2012/000095.
An International Preliminary Report on Patentability dated Aug. 21, 2013, which issued during the prosecution of Applicant's PCT/IL2012/000083.
An International Search Report and a Written Opinion both dated Oct. 4, 2012, which issued during the prosecution of Applicant's PCT/IL2012/000269.
An International Search Report and a Written Opinion both dated Aug. 31, 2012, which issued during the prosecution of Applicant's PCT/IL2012/000148.
An International Search Report and a Written Opinion both dated Sep. 6, 2012, which issued during the prosecution of Applicant's PCT/IL2012/000190.
An International Search Report and a Written Opinion both dated Sep. 24, 2012, which issued during the prosecution of Applicant's PCT/IL2012/00060.
An International Search Report and a Written Opinion both dated Oct. 1, 2012, which issued during the prosecution of Applicant's PCT/IL2012/000241.
An Office Action dated Oct. 11, 2012, which issued during the prosecution of U.S. Appl. No. 13/031,871.
U.S. Appl. No. 61/443,740, filed Feb. 17, 2011.
An Office Action dated Feb. 25, 2013, which issued during the prosecution of U.S. Appl. No. 13/031,871.
An Extended European Search Report dated Dec. 13, 2012, which issued during the prosecution of Applicant's European App No. 08719912.1.
Communication dated Feb. 3, 2015 from the United States Patent and Trademark Office in counterpart application No. 12/447,684.
Communication dated Nov. 28, 2014 from the European Patent Office in counterpart application No. 08861980.4.

* cited by examiner

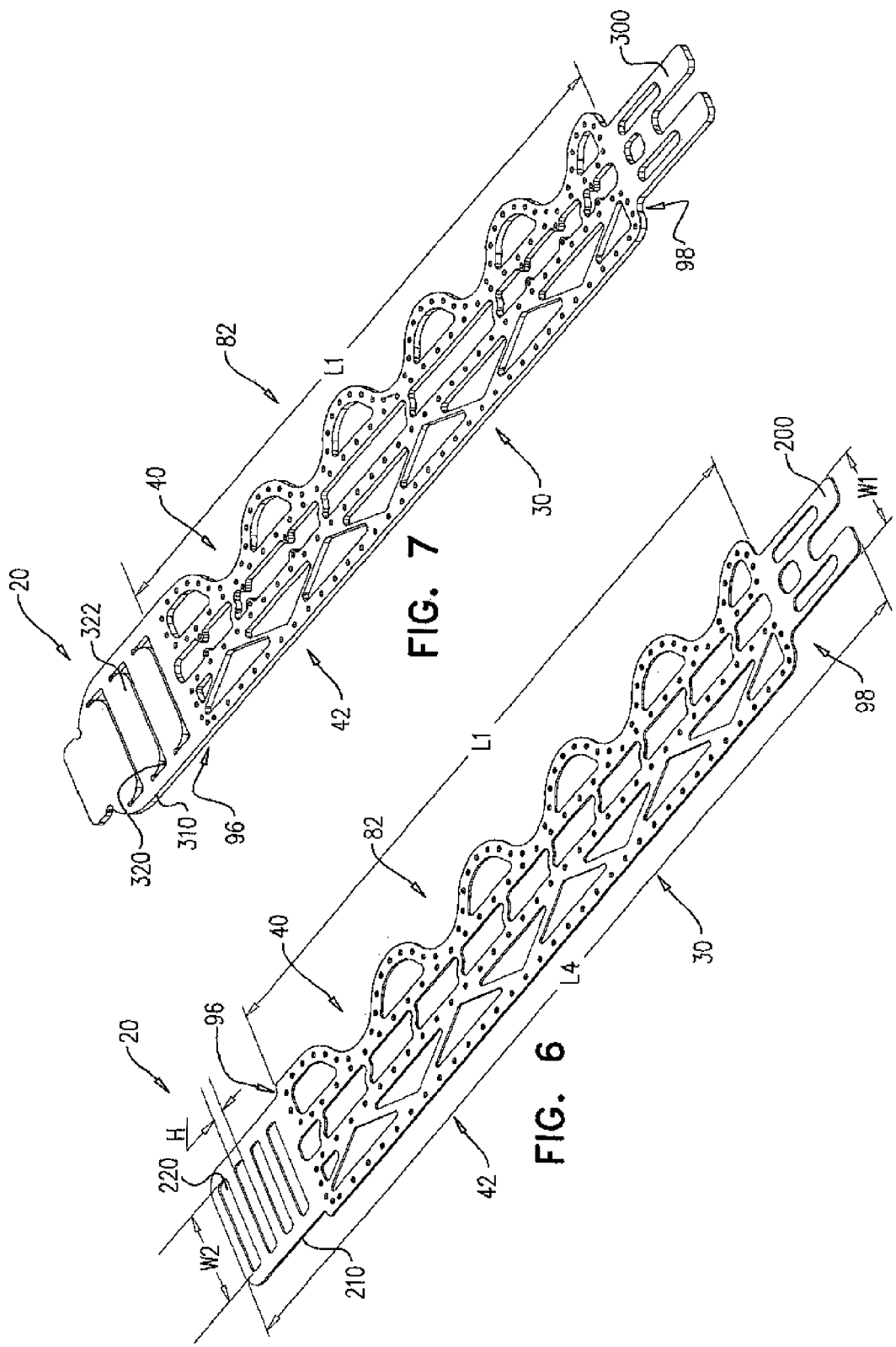

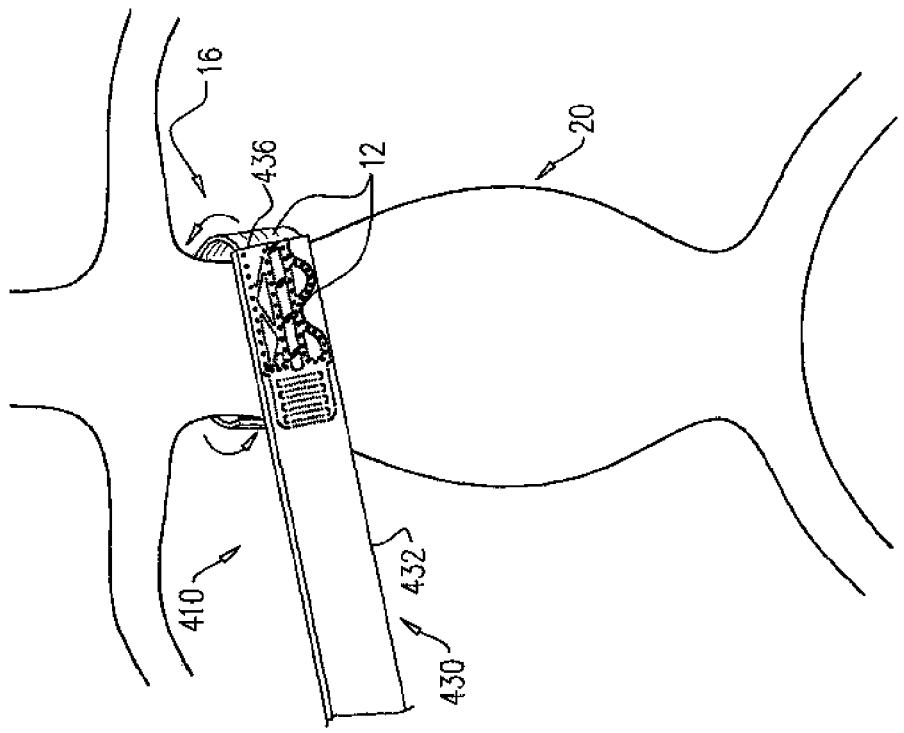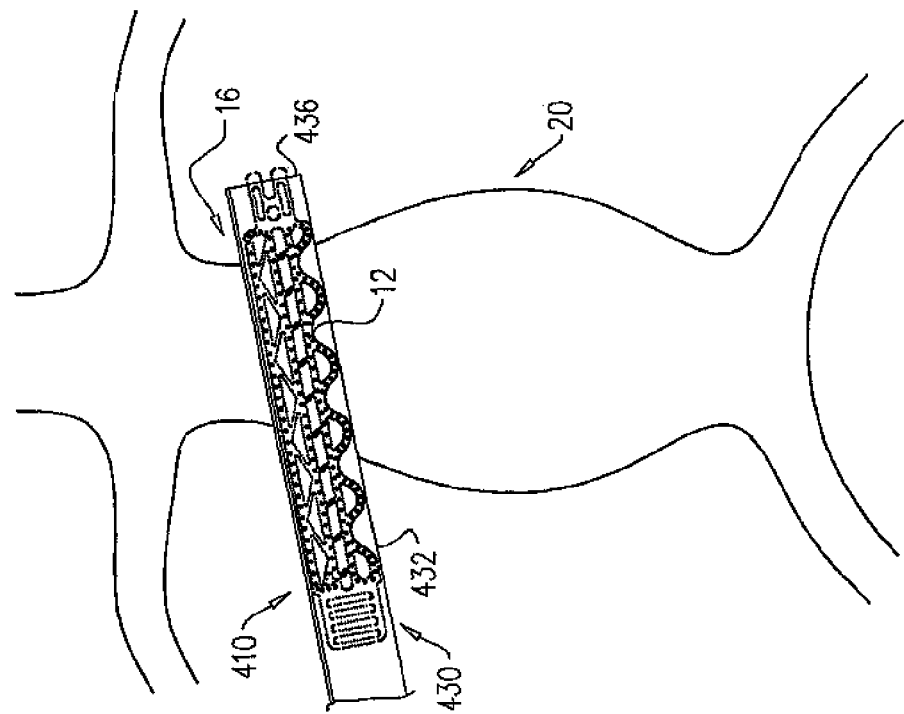

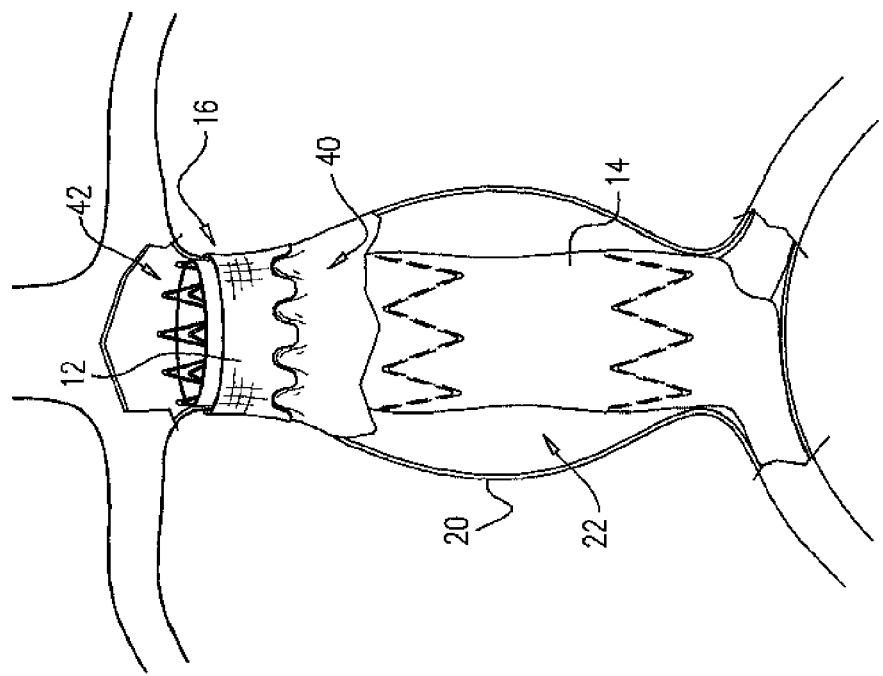
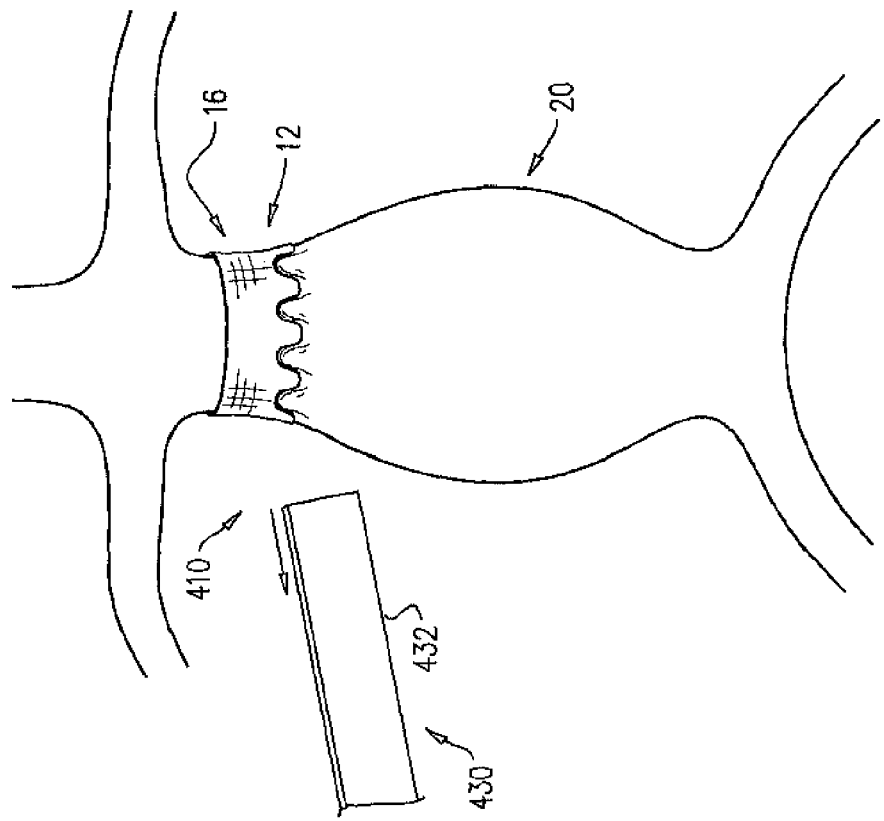

REDUCED-STRAIN EXTRA-VASCULAR RING FOR TREATING AORTIC ANEURYSM

CROSS REFERENCE TO RELATED APPLICATIONS

The present patent application is the US national stage of International Application PCT/IL2012/000095, filed Mar. 1, 2012, which claims priority from U.S Provisional Application No. 61/448,199, filed Mar. 2, 2011, which is assigned to the assignee of the present application and is incorporated herein by reference.

FIELD OF THE APPLICATION

The present invention relates generally to implantable medical devices, and specifically implantable vascular bands.

BACKGROUND OF THE APPLICATION

An aneurysm is a localized, blood-filled dilation (bulge) of a blood vessel caused by disease or weakening of the vessel wall. Left untreated, the aneurysm will frequently rupture, resulting in loss of blood through the rupture and death. Aneurysms are commonly classified by shape, structure and location. Aortic aneurysms are the most common form of arterial aneurysm and are life-threatening. It is common for an aortic aneurysm to occur in the portion of the abdominal aorta between the renal arteries and the iliac arteries. Aneurysms in the abdominal aorta are associated with particularly high mortality; accordingly, current medical standards call for urgent operative repair when aneurysm diameter is larger than 5 cm. Abdominal surgery, however, results in substantial stress to the body. Although the mortality rate for an aortic aneurysm is extremely high, there is also considerable mortality and morbidity associated with open surgical intervention to repair an aortic aneurysm.

Therefore, less invasive techniques have been developed to treat an aortic aneurysm without the attendant risks of intra-abdominal surgery. These techniques include transvascularly introducing an endovascular stent-graft into the aorta. The neck of the aorta at the cephalad end (i.e., above the aneurysm) is usually sufficient to maintain attachment of a stent-graft to the wall of the aorta. However, when an aneurysm is located near the iliac arteries, there may be an ill-defined neck or no neck below the aneurysm. Such an ill-defined neck may provide insufficient healthy aortic tissue to which to successfully mount a stent-graft. Furthermore, much of the abdominal aorta wall may be calcified which may make it difficult to attach the stent-graft to the aortic wall. Unfavorable anatomy relating to the neck of the aneurysm is the most common reason for patients being rejected for Endovascular Repair of Abdominal Aortic Aneurysm (EVAR). A short or absent infrarenal neck, large aortic diameters, and excessive angulation at this level are the main problems. Furthermore, progressive expansion of the aneurysm sac associated with type I endoleak can lead to compromise of the seal at the neck and is the principal indication for secondary intervention for this condition.

PCT Publication WO 2009/078010 to Shalev, and US Patent Application Publication 2010/0292774 in the national stage thereof, which are assigned to the assignee of the present application and is incorporated herein by reference, describe a system for treating an aneurysmatic abdominal aorta, comprising (a) an extra-vascular wrapping (EVW) comprising (i) at least one medical textile member adapted to at least partially encircle a segment of aorta in proximity to the renal arteries, and (ii) a structural member, wherein the EVW is adapted for laparoscopic delivery, and (b) an endovascular stent-graft (ESG) comprising (i) a compressible structural member, and (ii) a substantially fluid impervious fluid flow guide (FFG) attached thereto. Also described is an extra-vascular ring (EVR) adapted to encircle the neck of an aortic aneurysm. Further described are methods for treating an abdominal aortic aneurysm, comprising laparoscopically delivering the extra-vascular wrapping (EVW) and endovascularly placing an endovascular stent-graft (ESG). Also described are methods to treat a type I endoleak. U.S. Provisional Application 61/014,031, filed Dec. 15, 2007, from which the above-referenced applications claim priority, is also incorporated herein by reference.

SUMMARY OF THE APPLICATION

In some applications of the present invention, an extra-vascular ring is provided for deployment around a neck of an aneurysmal aorta, in order to create a generally cylindrical landing zone for an endovascular stent-graft. The endovascular stent-graft is endovascularly deployed in the aorta, spanning an aneurysm thereof, such that a portion of the endovascular stent-graft is positioned against an internal wall of aorta at the landing zone provided by the extra-vascular ring. The landing zone helps create a non-leaking seal between the stent-graft and the wall of the aorta. The extra-vascular ring thus helps secure the aneurismal neck from widening and/or leaking.

The extra-vascular ring is configured to evenly distribute the pressures and stresses on the partially-dilated tissue of the aortic aneurysm neck. To this end, a structural member of the ring is configured to assume an elongate hollow shape that has first and second longitudinal ends. At least the first longitudinal end has a profile that defines a series of curved portions and has no singularities or discontinuities, which profile extends around at least 50% of the first longitudinal end. The profile serves to homogeneously distribute the strain on the aortic tissue at the first longitudinal end of the ring. The profile provides spaces into which the excess circumference of the aorta can expand, rather than folding inwardly.

For some applications, the profile is a corrugated profile that defines a series of smooth undulations. For these applications, the smooth undulations are shaped so as to define alternating curved peaks and curved valleys. For some applications, the curved peaks are not sharp or traumatic; for example, they may have a radius of curvature equal to at least 3% of the length of the first longitudinal end, when the structural member is in a relaxed state. For some applications, the structural member comprises a plurality of stent struts.

Typically, the structural member is configured to generally not be longitudinally expansible if unrolled to a planar shape, one side of which is defined by the first longitudinal end of the structural member, and accordingly not to be radially expansible when the structural member has the elongate hollow shape. The alternating curved peaks and curved valleys of the corrugated profile of the longitudinal end are not configured to compress or stretch in a direction parallel to the longitudinal end. In other words, the curved peaks are not configured to bend or flex when the structural member is longitudinal stretched.

For some applications, such as in order to provide the longitudinal stability described in the previous paragraph, when the structural member has the planar shape, at least one of the stent struts extends completely alongside at least two of the undulations (i.e., two of the curved peaks and two of the curved valleys), such that the strut substantially prevents longitudinal stretching of the at least two of the undulations. For some applications, when the structural member has the planar shape, the strut has a length equal to at least 90% of the length of the first longitudinal end.

There is therefore provided, in accordance with an application of the present invention, apparatus for attachment to an aorta of a patient, the apparatus including:

an extra-vascular ring, which includes a structural member, which is configured to assume an elongate hollow shape, which has first and second longitudinal ends, and is suitable for placement at least partially around the aorta so as to provide a generally cylindrical landing zone; and an endovascular stent-graft, which is suitable for endovascular placement inside the aorta such that a portion of the endovascular stent-graft is positioned against an internal wall of the aorta at the landing zone provided by the structural member, wherein, if the structural member is unrolled to a planar shape, one side of the planar shape is defined by the first longitudinal end of the structural member, and at least the first longitudinal end has a profile that defines a series of curved portions and has no singularities or discontinuities, which profile extends along at least 50% of the first longitudinal end.

For some applications, the profile is a corrugated profile that defines a series of smooth undulations. For some applications, the corrugated profile has a substantially sinusoidal form.

For some applications, the first and second longitudinal ends are curved at least partially around a longitudinal axis defined by the elongate hollow shape, and the smooth undulations are shaped so as to define alternating curved peaks and curved valleys, which curved peaks extend in a direction away from the second longitudinal end and have a radius of curvature equal to at least 3% of a length of the first longitudinal end measured around the longitudinal axis, when the structural member is in a relaxed state.

For some applications, the smooth undulations are shaped so as to define alternating curved peaks and curved valleys, which curved peaks extend in a direction away from the second longitudinal end, and, if the structural member is unrolled to the planar shape, a radius of curvature of the curved peaks changes by less than 10% if the structural member, while having the planar shape, is longitudinally stretched from a relaxed state by application of a greatest force that is insufficient to cause plastic deformation of the structural member.

For some applications, the structural member includes a plurality of stent struts, and, if the structural member is unrolled to a planar shape, at least one of the stent struts extends completely alongside at least two of the undulations, such that the strut substantially prevents longitudinal stretching of the at least two of the undulations. For some applications, the at least one of the stent struts geometrically encompasses at least one straight line segment that is parallel to the one side and extends completely alongside the at least two of the undulations, when the structural member has the planar shape. For some applications, the at least one of the stent struts is straight when the structural has the planar shape. For some applications, the structural member has the planar shape, the at least one stent strut has a length, measured in a direction parallel to the one side, equal to at least 90% of a length of the one side.

For some applications, if the structural member is unrolled to the planar shape, the first longitudinal end of the structural member has a length that varies by less than 20% if the structural member, while having the planar shape, is longitudinally stretched from a relaxed state by application of a greatest force that is insufficient to cause plastic deformation of the structural member.

For some applications, the profile defines the series of curves interspersed with one or more straight portions.

For any of the applications described above, the structural member may be configured to assume the elongate hollow shape when in a relaxed state.

For any of the applications described above, the structural member may include a super-elastic material.

For any of the applications described above, the structural member may include a shape memory material.

For any of the applications described above, if the structural member is unrolled to the planar shape, the first longitudinal end may have a length that is equal to between 30 and 120 mm; and the elongate hollow shape may have a longitudinal length, measured parallel to a central longitudinal axis of the elongate hollow shape, that equals between 10 and 40 mm.

For any of the applications described above, the structural member, when having the elongate hollow shape, is shaped so as to define a gap that extends longitudinally along an entire longitudinal length of the elongate hollow shape from the first longitudinal end to the second longitudinal end. For some applications, the structural member is shaped so as to define (a) a first extension, which first extension defines at least one slot, and (b) a second extension, which is shaped so as to define a tab adapted to fit into the at least one slot, such that inserting the tab into the slot closes the gap. For some applications, the extra-vascular ring further includes one or more fastening elements for closing the gap.

For any of the applications described above, the apparatus may further include a hollow, generally tubular delivery shaft, in which the extra-vascular ring is removably disposed with the structural member in a deformed state. For some applications, the structural member is configured to automatically transition from the deformed state to a relaxed state as the structural member is deployed from the delivery shaft.

For any of the applications described above, the elongate hollow shape may be generally cylindrical.

There is further provided, in accordance with an application of the present invention, a method including:

providing an extra-vascular ring, which includes a structural member, which is configured to assume an elongate hollow shape, which has first and second longitudinal ends, wherein, if the structural member is unrolled to a planar shape, one side of the planar shape is defined by the first longitudinal end of the structural member, and at least the first longitudinal end has a profile that defines a series of curved portions and has no singularities or discontinuities, which profile extends along at least 50% of the first longitudinal end; and placing the extra-vascular ring at least partially around a neck of an aneurysmal aorta of a patient so as to provide a generally cylindrical landing zone, such that the profile homogenously distributes strain on aortic tissue at the first longitudinal end of the structural member.

For some applications, the method further includes placing an endovascular stent-graft inside the aorta such that a portion of the endovascular stein-graft is positioned against an internal wall of the neck at the landing zone provided by the structural member.

For some applications, placing the extra-vascular ring includes advancing, to an external surface of the aorta, a hollow, generally tubular delivery shaft, in which the extra-vascular ring is removably disposed with the structural member in a deformed state. For some applications, advancing the delivery shaft includes advancing the delivery shaft through a laparoscopic working channel to an abdominal location adjacent to renal arteries of the aorta, and laparoscopically placing the extra-vascular stent around the neck of the abdominal aorta in a vicinity of the renal arteries.

For some applications, placing the extra-vascular ring includes identifying the patient as suffering from an aneurysm of an abdominal aorta, and treating the aortic aneurysm by placing the extra-vascular ring at least partially around the neck of the abdominal aorta.

For some applications, providing the extra-vascular ring includes providing the extra-vascular ring in which the profile is a corrugated profile that defines a series of smooth undulations. For some applications, providing the extra-vascular ring includes providing the extra-vascular ring in which the corrugated profile has a substantially sinusoidal form.

For some applications, providing the extra-vascular ring includes providing the extra-vascular ring in which the first and second longitudinal ends are curved at least partially around a longitudinal axis defined by the elongate hollow shape, and the smooth undulations are shaped so as to define alternating curved peaks and curved valleys, which curved peaks extend in a direction away from the second longitudinal end and have a radius of curvature equal to at least 3% of a length of the first longitudinal end measured around the longitudinal axis, when the structural member is in a relaxed state.

For some applications, providing the extra-vascular ring includes providing the extra-vascular ring in which the smooth undulations are shaped so as to define alternating curved peaks and curved valleys, which curved peaks extend in a direction away from the second longitudinal end, and wherein, if the structural member is unrolled to the planar shape, a radius of curvature of the curved peaks changes by less than 10% if the structural member, while having the planar shape, is longitudinally stretched from a relaxed state by application of a greatest force that is insufficient to cause plastic deformation of the structural member.

For some applications, providing the extra-vascular ring includes providing the extra-vascular ring in which the structural member includes a plurality of stent struts, and, if the structural member is unrolled to the planar shape, at least one of the stent struts extends completely alongside at least two of the undulations, such that the strut substantially prevents longitudinal stretching of the at least two of the undulations. For some applications, providing the extra-vascular ring includes providing the extra-vascular ring in which the at least one of the stent struts geometrically encompasses at least one straight line segment that is parallel to the one side and extends completely alongside the at least two of the undulations, when the structural member has the planar shape. For some applications, providing the extra-vascular ring includes providing the extra-vascular ring in which the at least one of the stent struts is straight when the structural has the planar shape. For some applications, providing the extra-vascular ring includes providing the extra-vascular ring in which, when the structural member has the planar shape, the at least one stent strut has a length, measured in a direction parallel to the one side, equal to at least 90% of a length of the one side.

For some applications, providing the extra-vascular ring includes providing the extra-vascular ring characterized in that, if the structural member is unrolled to the planar shape, the first longitudinal end of the structural member has a length that varies by less than 20% if the structural member, while having the planar shape, is longitudinally stretched from a relaxed state by application of a greatest force that is insufficient to cause plastic deformation of the structural member.

For some applications, providing the extra-vascular ring includes providing the extra-vascular ring in which the profile defines the series of curved portions interspersed with one or more straight portions.

For some applications, providing the extra-vascular ring includes providing the extra-vascular ring in which the structural member is configured to assume the elongate hollow shape when in a relaxed state.

For some applications, providing the extra-vascular ring includes providing the extra-vascular ring in which the elongate hollow shape is generally cylindrical.

The present invention will be more fully understood from the following detailed description of embodiments thereof, taken together with the drawings, in which:

BRIEF DESCRIPTION OF THE DRAWINGS

FIG. 6 is a schematic illustration of another configuration of the structural member of the extra-vascular ring of FIG. 2 in the planar unrolled state, in accordance with an application of the present invention;

FIG. 7 is a schematic illustration of yet another configuration of the structural member of the extra-vascular ring of FIG. 2 in the planar unrolled state, in accordance with an application of the present invention;

FIGS. 9A-D are schematic illustrations of a delivery system and method for delivering the extra-vascular ring of FIG. 2 around an aorta, in accordance with an application of the present invention.

DETAILED DESCRIPTION OF APPLICATIONS

Figure 1:
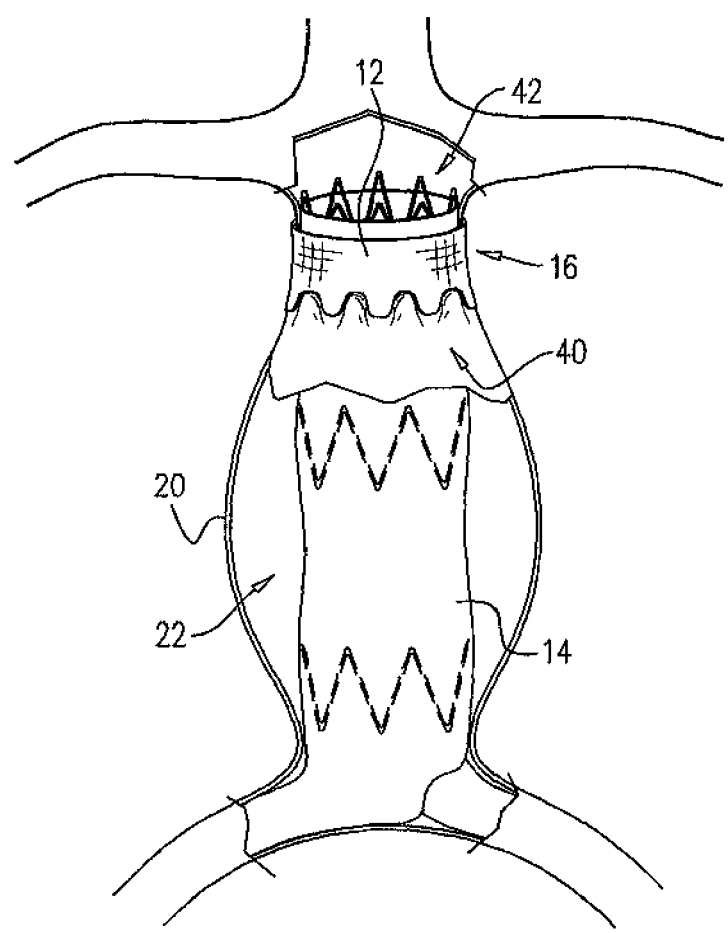
FIG. 1 is a schematic illustration of an endovascular stent-graft system, in accordance with an application of the present invention.

FIG. 1 is a schematic illustration of an endovascular stent-graft system 10, in accordance with an application of the present invention. System 10 comprises an extra-vascular ring 12 and, for some applications, an endovascular stent-graft 14. When deployed around a neck 16 of an aneurysmal aorta 20, extra-vascular ring 12 creates a generally cylindrical landing zone for endovascular stent-graft 14 (which optionally is bifurcated, as shown). As shown in FIG. 1, endovascular stent-graft 14 is endovascularly deployed in aorta 20, spanning an aneurysm 22 thereof, such that a portion (e.g., a superior distal portion) of endovascular stent-graft 14 is positioned against an internal wall of aorta 20 at the landing zone provided by the extra-vascular ring. The landing zone helps create a non-leaking seal between the stent-graft and the wall of the aorta. Extra-vascular ring 12 thus helps secure the aneurismal neck from widening and/or leaking. Typically, the landing zone is generally resistant to dilation. Extra-vascular ring 12 comprises a structural member 30 and, optionally, a textile member 402, such as described hereinbelow with reference to FIGS. 8A-B.

Figure 2:
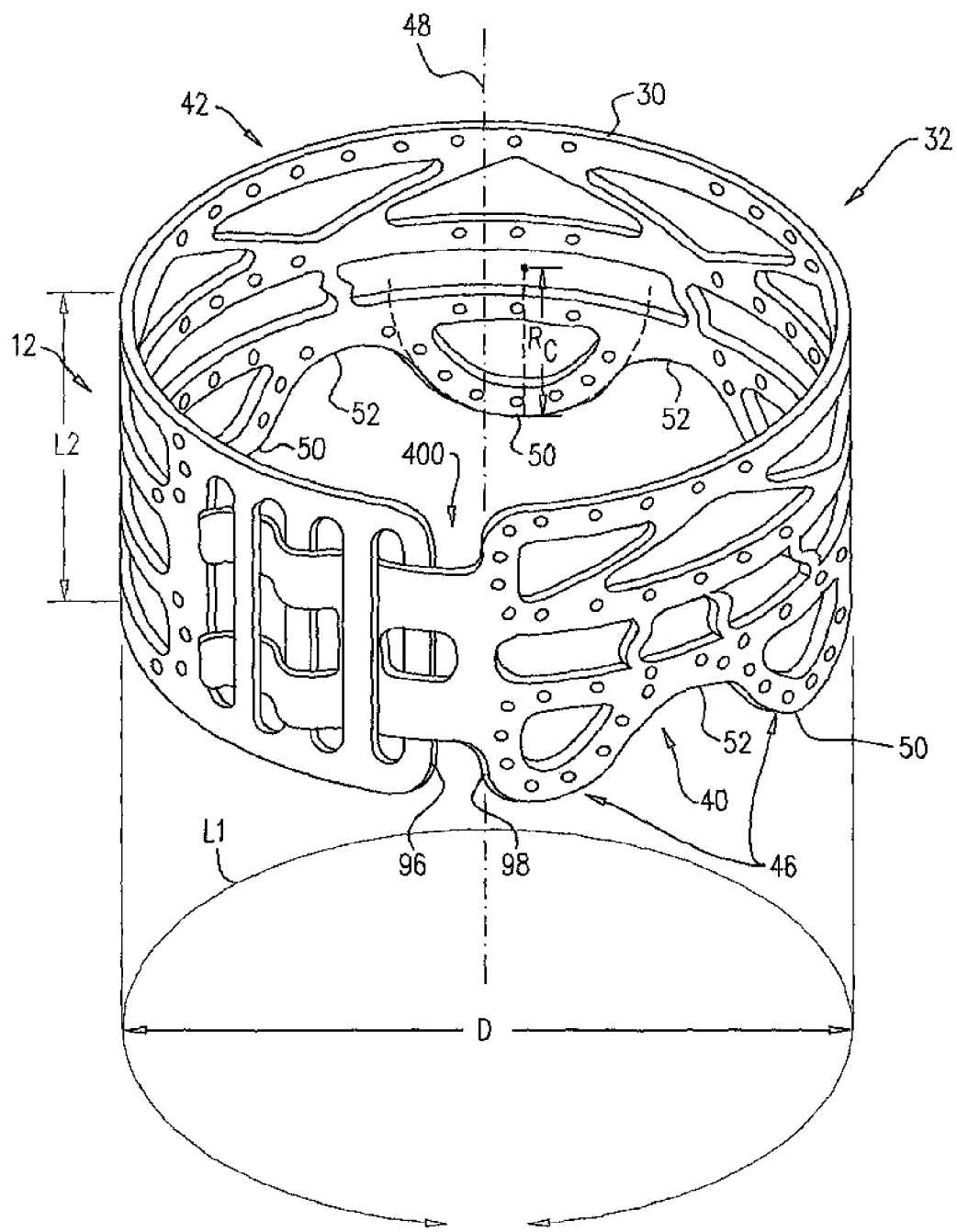
FIG. 2 is a schematic illustration of a structural member of an extra-vascular ring of the endovascular stent-graft system of FIG. 1, in accordance with an application of the present invention.

FIG. 2 is a schematic illustration of structural member 30 of extra-vascular ring 12, in accordance with an application of the present invention. Structural member 30 is configured to assume an elongate hollow shape 32, as shown in FIG. 2, which, for example, may be generally cylindrical. Elongate hollow shape 32 is suitable for placement at least partially around aorta 20 so as to provide the landing zone. Elongate hollow shape 32 has first and second longitudinal ends 40 and 42. Extra-vascular ring 12 is configured to be placed around aorta 20 oriented with first longitudinal end 40 inferior to second longitudinal end 42, typically with first longitudinal end 40 positioned at an inferior end of neck 16 and second longitudinal end 42 positioned at a superior end of neck 16.

At least first longitudinal end 40 of structural member 30 has a profile that defines a series of curved portions and has no singularities or discontinuities, which profile extends around at least 50% of first longitudinal end 40 (i.e., along at least 50% of a length L1 of first longitudinal end 40 measured around elongate hollow shape 32), such as at least 75%, or 100%. The curved portions rise and fall with respect to a direction that is parallel to a longitudinal axis 48 defined by the elongate hollow shape 32. Equivalently, if structural member 30 is unrolled to a planar shape 82, such as described hereinbelow with reference to FIGS. 5-7, one side of planar shape 82 is defined by first longitudinal end 40, and at least first longitudinal end 40 has the profile that defines the series of curved portions and has no singularities or discontinuities, and the profile extends along at least 50% of first longitudinal end 40, such as at least 75%, or 100%.

For some applications in which the profile extends around or along (depending on whether the structural member is rolled or unrolled) less than 100% of first longitudinal end 40, the profile is provided along two or more portions that are non-contiguous around or along the first longitudinal end. For example, the profile may be provided along two portions that are non-contiguous with each other, each of which extends around or along between 20% and 40% of first longitudinal end 40. For other applications in which the profile extends around or along less than 100% of first longitudinal end 40, the corrugate profile is provided on a single contiguous portion around or along a portion of the first longitudinal end. Typically, any portions of first longitudinal end 40 along which the profile is not provided are not shaped to have any singularities, discontinuities, or sharp changes in direction, e.g., are straight if structural member 30 is unrolled to planar shape 82, such as described hereinbelow with reference to FIGS. 5-7.

For some applications, the profile is a corrugated profile that defines a series of smooth undulations 46. As used herein, including in the claims, the term "corrugated" means having any shape comprising a series of smooth undulations that have no singularities, discontinuities, or sharp changes in direction. Therefore, the corrugated profile does not include any sharp, and thus traumatic, features. For example, the term "corrugated" does not include within its scope sawtooth and square-wave forms. The corrugated profile is provided along first longitudinal end 40 as described in the previous paragraph. For some applications, the corrugated profile has a substantially sinusoidal form (which includes the series of curved portions). Alternatively or additionally, for some applications, at least first longitudinal end 40 of structural member 30 has a waved profile.

As can be seen in FIG. 2, first and second longitudinal ends 40 and 42 are curved at least partially around longitudinal axis 48. Smooth undulations 46 of first longitudinal end 40 are shaped so as to define alternating curved peaks 50 and curved valleys 52. Peaks 50 extend in a direction away from second longitudinal end 42. (Each of the smooth undulations is shaped so as to define exactly one of curved peaks 50 adjacent to exactly one of curved valleys 52.) For some applications, the corrugated profile is shaped so as to define at least 3, no more than 10, and/or between 3 and 10 undulations 46, each of which undulations is shaped so as to define exactly one curved peak 50 and exactly one curved valley 52. For some applications, curved peaks 50 do not include any straight portions. Alternatively or additionally, for some applications, curved valleys 52 do not include any straight portions.

For some applications, curved peaks 50 are not sharp or traumatic; for example, they may have a radius of curvature $R_C$ equal to at least 1.5% (e.g., at least 3%) of length L1 of first longitudinal end 40 measured around longitudinal axis 48, when structural member 30 is in a relaxed state (radius of curvature $R_C$ is measured along the outer surface of the curved peak, as indicated in FIG. 2). (Length L1 is circumferential, i.e., curved, when structural member 30 has elongate hollow shape 32, as shown in FIG. 2. The length is also labeled in FIG. 5, in which the structural member is shown in a planar unrolled state.) For some applications, length L1 is at least 30 mm, no more than 120 mm, and/or between 30 and 120 mm, such as 85 mm. For example, length L1 may be 80 mm, in which case radius of curvature $R_C$ may be at least 1.27 mm. For some applications, elongate hollow shape 32 has a longitudinal length (measured parallel to longitudinal axis 48) of at least 10 mm, no more than 40 mm, and/or between 10 and 40 mm, such as 15 mm.

Elongate hollow shape 32 has an inner diameter D suitable for surrounding a vessel, such as an aorta, e.g., a descending aorta, such as for treating an aortic aneurysm, i.e., large enough to surround the aorta at the point of attachment of extra-vascular ring 12 and small enough such that upon closure, the inner surface of the elongate hollow shape 32 (which may be cylindrical, as mentioned above) makes direct or indirect contact at least partially with the outer surface of the aorta being treated. For applications in which extra-vascular ring 12 further comprises a textile member 402, such as described hereinbelow with reference to FIGS. 8A-B, elongate hollow shape 32 makes indirect contact at least partially with the outer surface of the aorta being treated, via the textile member. For example, inner diameter D may be at least 2 cm, no more than 4 cm, and/or between 2 and 4 cm. For some applications, radius of curvature $R_C$ of curved peaks 50 is equal to at least 5% (e.g., at least 10%) of inner diameter D when ring 12 is placed around neck 16.

Figure 3A:
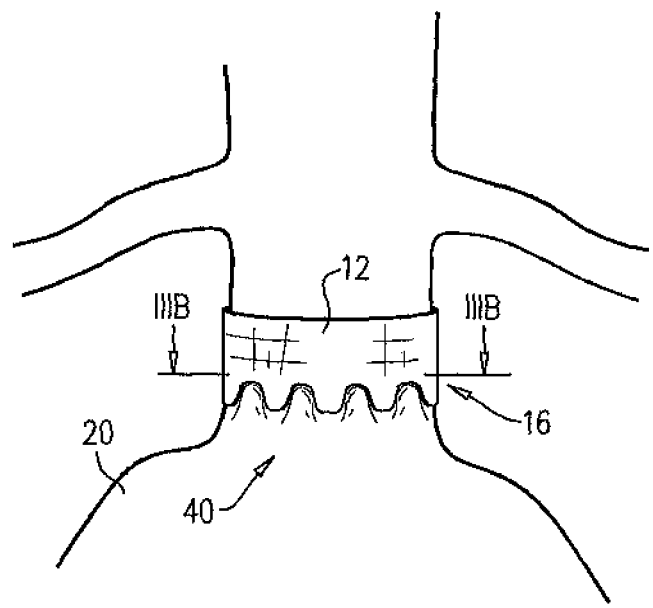
FIGS. 3A-B are schematic illustrations of the extra-vascular ring of FIG. 2 deployed around a neck of an aneurysmal aorta, in accordance with an application of the present invention.
Figure 3B:
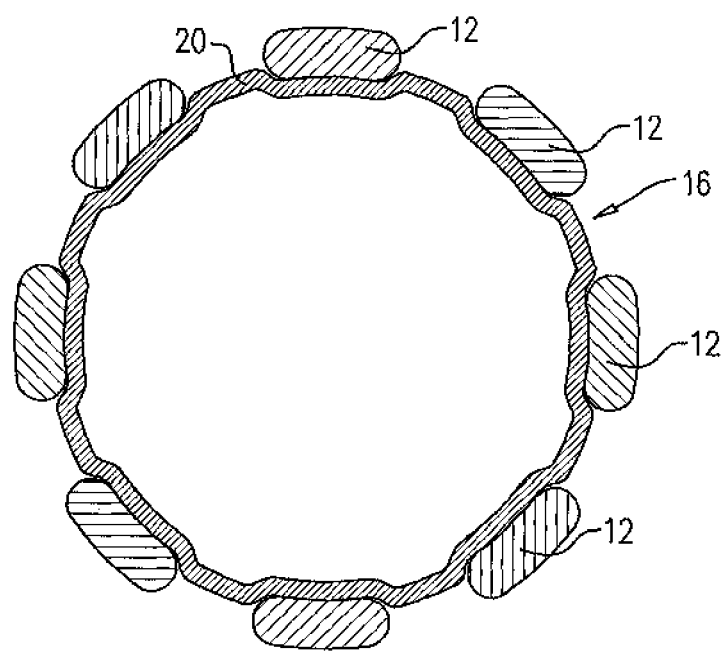

Reference is now made to FIGS. 3A-B, which are schematic illustrations of extra-vascular ring 12 deployed around neck 16 of aneurysmal aorta 20, in accordance with an application of the present invention. FIG. 3B is a cross-sectional view of ring 12 and aorta 20 along line IIIB-IIIB of FIG. 3A. The corrugated profile of longitudinal end 40 serves to evenly distribute the pressures and stresses on the partially-dilated tissue of neck 16, in particular on the section of the aorta in the vicinity of longitudinal end 40 of ring 12. The corrugated profile serves to homogeneously distribute the strain on the aortic tissue at the first longitudinal end of the ring. As can be seen in FIGS. 3A-B, the corrugated profile effectively diffuses the strain on the aortic wall. The corrugated profile provides spaces into which the excess circumference of the aorta can expand, rather than folding inwardly as described hereinbelow with reference to FIGS. 4A-B.

Figure 3C:
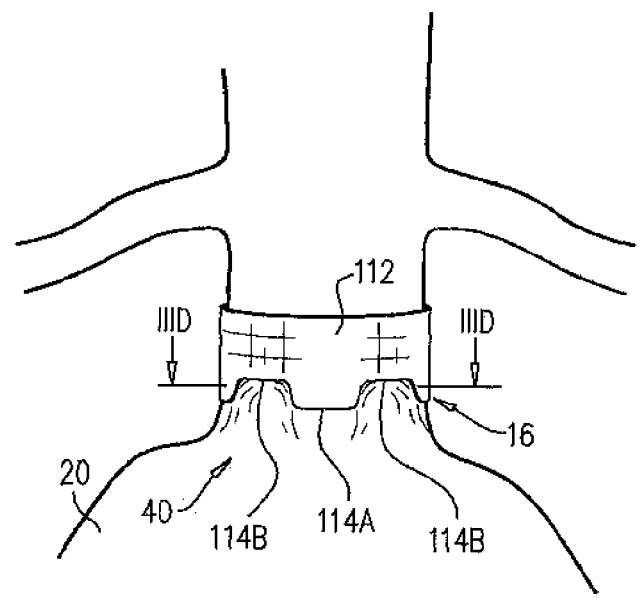
FIGS. 3C-D are schematic illustrations of another extra-vascular ring deployed around a neck of an aneurysmal aorta, in accordance with an application of the present invention.
Figure 3D:
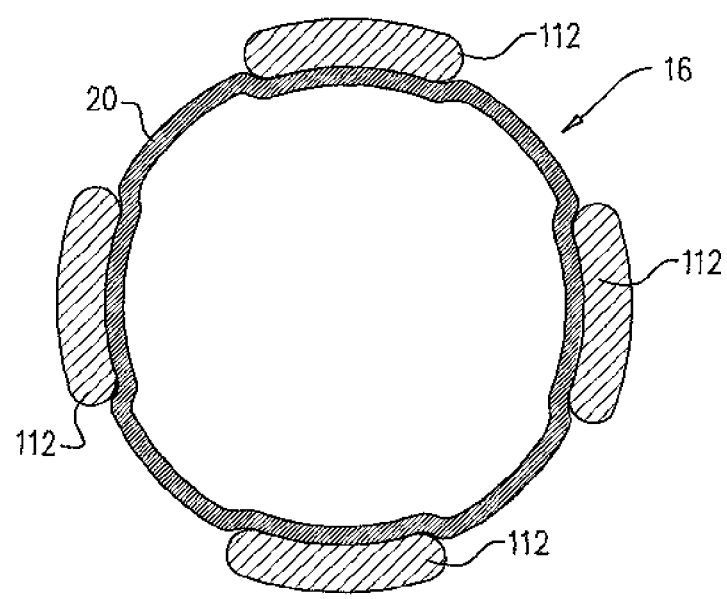

Reference is made to FIGS. 3C-D, which are schematic illustrations of an extra-vascular ring 112 deployed around neck 16 of aneurysmal aorta 20, in accordance with an application of the present invention. FIG. 3D is a cross-sectional view of ring 112 and aorta 20 along line IIID-IIID of FIG. 3C. Other than as described below, extra-vascular ring 112 is generally similar to extra-vascular ring 12 described hereinabove and hereinbelow, and may include any of the features of extra-vascular ring 12 described hereinabove and/or hereinbelow. The profile of first longitudinal end 40 of extra-vascular ring 112 includes the series of curved portions interspersed with one or more straight portions 114. The profile does not have any sharp changes in direction. For example, one or more peaks of the undulations may be shaped so as to define a straight portion 114A, and/or one or more valleys of the undulations may be shaped so as to define a straight portion 114B. It is noted that the profile of first longitudinal end 40 of extra-vascular ring 112 is not a square-wave form, because there are no sharp changes in direction, such as right angles, in the profile. The profile of longitudinal end 40 serves to minimize the pressures and stresses on the tissue of the aorta, in particular on the section of the aorta in the vicinity of longitudinal end 40 of ring 112. The profile serves to homogeneously diffuse the strain on the aortic tissue at the longitudinal ends of the ring. As can be seen in FIGS. 3C-D, the profile effectively diffuses the strain on the aortic wall. The profile provides spaces into which the excess circumference of the aorta can expand, rather than folding inwardly as described hereinbelow with reference to FIGS. 4A-B.

Figure 4A:
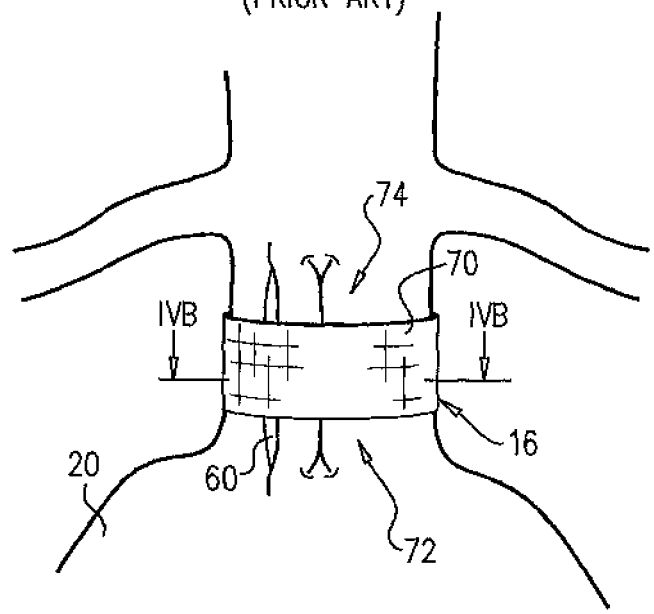
FIGS. 4A-B are schematic illustrations of an extra-vascular ring deployed around a neck of an aneurysmal aorta, as known in the prior art.
Figure 4B:
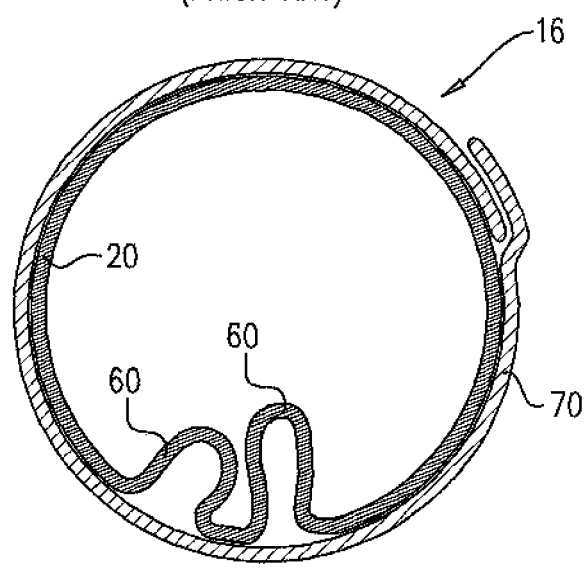

Reference is made to FIGS. 4A-B, which are schematic illustrations of an extra-vascular ring 70 deployed around neck 16 of aneurysmal aorta 20, as known in the prior art. FIG. 4B is a cross-sectional view of ring 70 and aorta 20 along line IVB-IVB of FIG. 4A. Both longitudinal ends 72 and 74 of ring 70 have a straight profile, as known in the prior art. As can be seen, in order to close ring 70, it is necessary to place a substantial amount of strain on aorta 20. As shown in FIG. 4B, this strain can lead to collapse or deformation of part of the aortic wall, which may result, for example, in one or more portions 80 of the wall folding inwardly.

Figure 5:
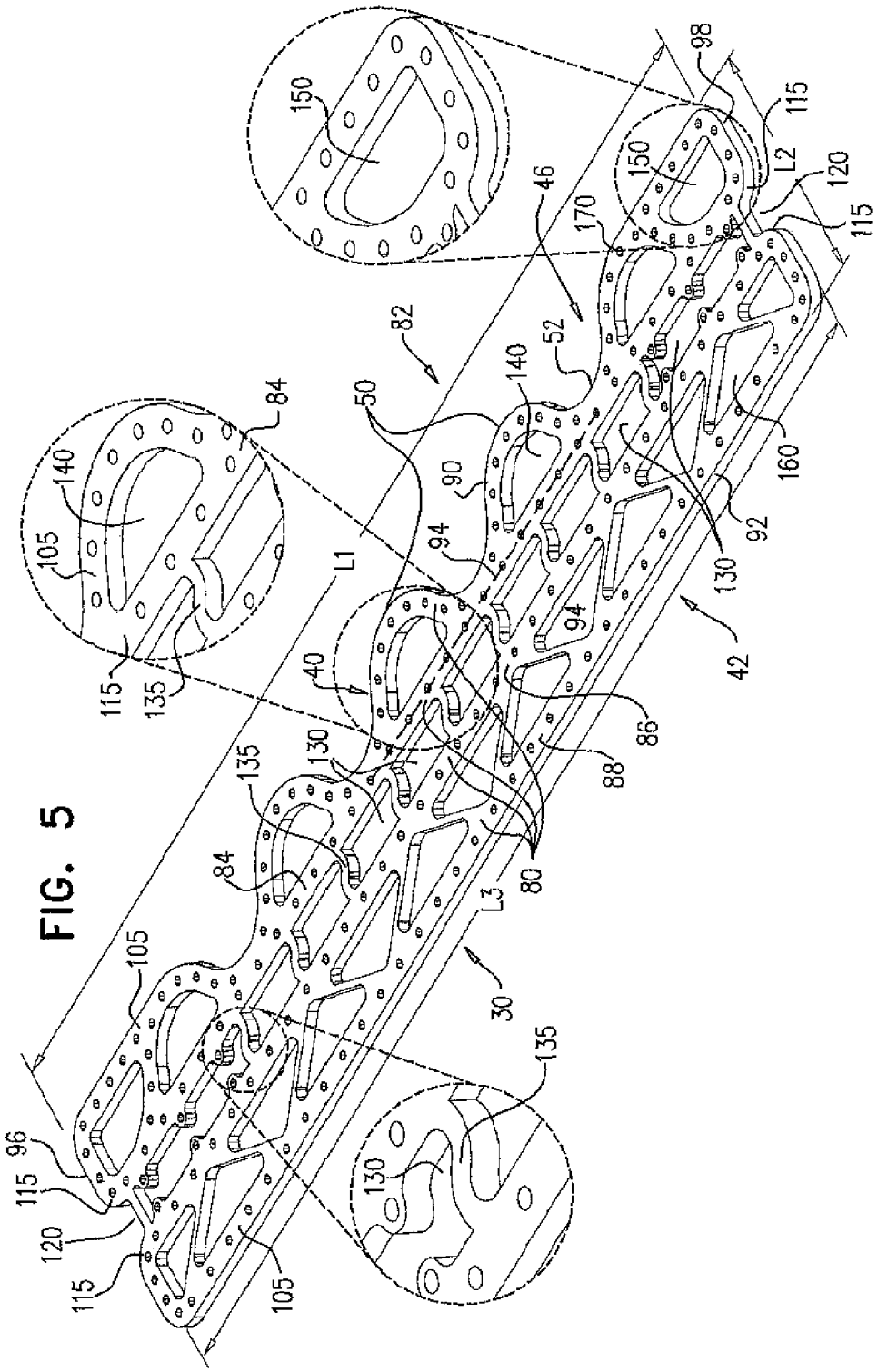
FIG. 5 is a schematic illustration of a structural member of the extra-vascular ring of FIG. 2 in a planar unrolled state, in accordance with an application of the present invention.

Reference is again made to FIGS. 1, 2, and 3A-B, and additionally to FIG. 5, which is a schematic illustration of structural member 30 of extra-vascular ring 12 in a planar unrolled state, in accordance with an application of the present invention. Extra-vascular ring 12 is shown in a relaxed state in FIG. 5. Typically, extra-vascular ring 12 is configured to transition between the open planar unrolled state shown in FIG. 5 (or the other configurations described hereinbelow with reference to FIG. 6 or 7), and the rolled state shown in FIGS. 1, 2, and 3A-B. For some applications, extra-vascular ring 12 is placed in the planar unrolled state for delivery in a catheter to the extra-aortic site, such as described hereinbelow with reference to FIG. 9A, and transitions (typically, automatically) to the rolled state around the aorta upon being deployed from the catheter, such as described hereinbelow with reference to FIGS. 9B-C.

Structural member 30 of ring 12 comprises a material suitable for use in treatment of aortic aneurysms and that is capable of being transitioned between an open planar state and a rolled state. For some applications, structural member 30 comprises a shape-memory material or a superelastic material. For example, the shape-memory material may comprise a nickel-titanium alloy such as Nitinol, (which is also super-elastic over a defined temperature range). For some applications, structural member 30 is configured to assume the rolled, elongate hollow shape when in a relaxed state. For some applications, structural member 30, while in its open planar state is rolled into a ring (such as shown in FIG. 2) of a desired diameter and then heated to fix its dimensions (optionally, the structural member is quickly quenched, e.g., in water, to prevent aging effects).

Alternatively, structural member 30 comprises another material with properties that make it suitable for treatment of aortic aneurysm. Non-limiting examples of such properties include biocompatibility, tensile strength, flexibility, and workability. For some applications, the structural member comprises one or more of these materials (e.g., a biocompatible polymer), and is introduced into the patient by rolling the structural member into a cylinder of small enough diameter to enable introduction by laparoscopic methods, unrolling it in situ, wrapping it around the aorta, and securing it, such as using any of the methods described hereinbelow.

For some applications, structural member 30 comprises a plurality of stent struts 80. For some applications, the stent struts have a thickness of between 0.1 and 1 mm, such as 0.30 mm.

If structural member 30 is unrolled to planar shape 82, such as shown in FIG. 5, one side 90 of the planar shape is defined by first longitudinal end 40 of structural member 30, and another side 92 of the planar shape is defined by second longitudinal end 42 of structural member 30.

For some applications, length L1 of side 90 (corresponding to first longitudinal end 40) varies by less than 20% (e.g., less than 10%) if the structural member, while having planar shape 82, is longitudinally stretched from a relaxed state by application of a greatest force that is insufficient to cause plastic deformation of the structural member. (Application of a force greater than this greatest force will result in plastic deformation of the structural member, in which case the length might increase substantially before breaking.) In other words, structural member 30 is configured to generally not be longitudinally expansible when it has planar shape 82, and accordingly not to be radially expansible when it has elongate hollow shape 32. Alternating curved peaks 50 and curved valleys 52 of the corrugated profile of longitudinal end 40 are not configured to compress or stretch in a direction parallel to longitudinal end 40. (In order to clarify the term "parallel" in this context, it is noted that undulations 46 of the corrugated profile are disposed about a straight line when the structural member has planar shape 82; the direction is parallel to this line; the term "parallel" should also be understood in this way hereinbelow and in the claims.) For some applications, radius of curvature $R_C$ of curved peaks 50 changes by less than 10% (e.g., less than 5%) if the structural member, while having planar shape 82, is longitudinally stretched from a relaxed state by application of a greatest force that is insufficient to cause plastic deformation of the structural member. In other words, curved peaks 50 are not configured to bend or flex when the structural member is longitudinal stretched.

For some applications, such as in order to provide the longitudinal stability described in the previous paragraph, when structural member 30 has planar shape 82, at least one 84 of stent struts 80 extends completely alongside at least two of undulations 46 (i.e., two of curved peaks 50 and two of curved valleys 52), such that strut 84 substantially prevents longitudinal stretching of the at least two of the undulations. For some applications, when structural member 30 has planar shape 82, strut 84 has a length L3, measured in a direction parallel to side 90, equal to at least 90% of length L1 of side 90, such as equal to length L1. For some applications, a plurality of stent struts 80 extend completely alongside at least two of undulations 46, such as two of stent struts 80, or three of stent struts 80, as labeled struts 84, 86, and 88 in FIG. 5.

For some applications, stent strut 84 geometrically encompasses at least one straight line segment 94 that is parallel to side 90 and extends completely alongside the at least two of undulations 46, when structural member 30 has planar shape 82. In other words, strut 84 is shaped such that a straight line segment could be drawn on the strut completely alongside the at least two of undulations 46. It is to be understood that straight line segment 94 is an abstract geometric construct provided for purposes of describing the shape of strut 84, rather than a physical element of structural member 30, and thus is typically not actually drawn on the structural member. For some applications, stent strut 84 is straight when structural member 30 is unrolled to planar shape 82.

Reference is still made to FIG. 5. For some applications, planar shape 82 of extra-vascular ring 12 is generally rectangular, with two substantially parallel short sides 96 and 98 and two long sides 90 and 92, each of which is substantially perpendicular to the short sides. For some applications, side 92 (i.e., the side not shown as corrugated) is straight. In other embodiments, both long sides 90 and 92 have respective corrugated profiles along at least 50% of their respective lengths, such as along at least 75%, e.g., 100%, of their respective lengths (configuration not shown). For some applications, planar shape 82 has rounded corners, as shown in FIG. 5 (and FIGS. 6 and 7).

For some applications, the edges of stent struts 80 are at least partially rounded smooth, such as by chemical erosion or electro-chemical erosion, as is known in the stent art. For clarity of illustration, this rounding is not shown in FIG. 5 (or FIGS. 2, 6, 7, and 8A-B).

Reference is again made to FIG. 2. For some applications, longitudinal axis 48 is substantially parallel to short sides 96 and 98 of structural member 30, and long sides 90 and 92 form upper and lower faces of elongate hollow shape 32; for applications in which elongate hollow shape 32 is cylindrical, the long sides form the (open) circular upper and lower faces of the cylinder. As a result, the corrugated profile is transverse to longitudinal axis 48 when structural member 30 is in its rolled state. As described below, the ring is brought to its final diameter after its insertion into the patient's body.

Reference is again made to FIG. 5. For some applications, stent struts 80 are shaped so as to define a plurality of missing portions of structural member 30, i.e., openings through structural member 30. In the exemplary configuration shown in FIG. 5, structural member 30 is shaped so as to define an outer substantially contiguous border 105, which may, for example have a width of about 1.50±0.05 mm. In each of respective central portions 120 (typically the central 3 ram) of short sides 96 and 98, border 105 is recessed by two rounded portions 115, and may be narrower than the remainder of the border (e.g., 0.7 mm in width).

For some applications, a central portion of structural member is shaped so as to define a plurality of missing portions 130, two sides of which missing portions are substantially parallel to long side 92. A blow-up in FIG. 5 shows a detailed view of the edge of one of these missing portions 130, including a separating stent strut 135 between them (in the configuration shown, this separating stent strut is curved and has a typical width of about 0.7 mm).

For some applications, structural member 30 is shaped so as to define missing portions 140 along long side 90 (which has the profile), between undulations 46 and stent strut 84 (described above). For some applications, structural member 30 is shaped so as to define two missing portions 150 nearest short sides 96 and 98, each of which may have the shape of a rectangle truncated by a curve along the side nearest first missing portion 140. Detailed views of missing portions 140 and 150 are shown in respective blow-ups in FIG. 5, in accordance with respective applications of the present invention.

For some applications, structural member 30 is shaped so as to define a series of triangular missing portions 160 with one side parallel to long side 92 and having alternating orientations, between central missing portions 130 and the inside of border 105 (e.g, between struts 86 and 88, described hereinabove).

For some applications, structural member 30 is shaped so as to define a plurality of small (e.g., circular) missing portions 170, which may, for example have a typical diameter of 0.5+/−0.1 mm. For some applications, missing portions 170 are located on all areas of the structural member at which the material has a width sufficient to support these missing portions. Optionally, missing portions 170 are substantially centered with respect to the width of stent struts 80.

For some applications, the missing portions described above serve one or more of four purposes. First, the missing portions may reduce the weight of structural member 30. Second, the missing portions may reduce the amount of material needed to construct structural member 30. Third, the missing portions may allow free tissue ingrowth therethrough. Fourth, the missing portions may be arranged to enhance flexibility of the structural member. It is to be understood that the particular arrangement of missing portions 130 and 170 are shown in the figures by way of example and not limitation, and that other arrangements that achieve the same or similar purposes will be apparent to those skilled in the art who have read the present application, and are within the scope of the present invention.

Reference is now made to FIG. 6, which is a schematic illustration of another configuration of structural member 30 of extra-vascular ring 12 in the planar unrolled state, in accordance with an application of the present invention. In this configuration, structural member 30 comprises, in addition to the elements described above with reference to FIGS. 1, 2, 3A-B, and 5, a tab 200 at one of short sides 96 and 98, and an extension 210 at the other one of short sides 96 and 98. Extension 210 is shaped so as to define a plurality of slots 220. For some applications, an overall length L4 of structural member 30, including tab 200 and extension 210 is at least 30 mm, no more than 150 mm, and/or between 30 and 150 mm, such as about 108 mm; for example, the tab may add about 13 mm to the length of the structural member, and the extension may add about 10 to 20 mm. For some applications, a width W1 of the tab is about 8.75 mm, a width W2 of slots 220 is about 12 mm, and a height H of the slots is about 1.5 mm. (Length L1 of first longitudinal end 40 is to be understood herein, including in the claims, as excluding the length of tab 200 and the length of extension 210.)

Reference is now made to FIG. 7, which is a schematic illustration of yet another configuration of structural member 30 of extra-vascular ring 12 in the planar unrolled state, in accordance with an application of the present invention. As in the configuration described hereinabove with reference to FIG. 6, in this configuration structural member 30 comprises a tab-and-slot assembly, which includes a tab 300 and an extension 310.

Extension 310 is shaped so as to define slots 320 that include respective flexible flaps 322 that aid in securing tab 300 when the ring is closed. Typically, the overall dimensions of the configuration of FIG. 7 are substantially the same as those of the configuration of FIG. 6. (Length L1 of first longitudinal end 40 is to be understood herein, including in the claims, as excluding the length of tab 300 and the length of extension 310.)

Reference is made to FIGS. 2, 5, 6, and 7. For some applications, when extra-vascular ring 12 is brought from its planar, unrolled open state (such as shown in FIGS. 5, 6, and 7) to its rolled state (such as shown in FIG. 2), a gap 400 remains between short sides 96 and 98. When structural member 30 has elongate hollow shape 32, gap 400 typically extends longitudinally along an entire longitudinal length of elongate hollow shape 32 from first longitudinal end 40 to second longitudinal end 42. Short sides 96 and 98 are not brought into contact with each other, and the ring is not otherwise closed, until the ring has been put in place around the patient's aorta. Instead the final closure of the ring (which closes gap 400) is effected after the ring has been put into place around the patient's aorta. In the case of the configuration described with reference to FIG. 6, the closure is effected by inserting tab 200 into slots 220, while in the case of the configuration described with reference to FIG. 7, the closure is effected by inserting tab 300 into slots 320.

Reference is now made to FIGS. 1-3D and 5-7. Structural member 30 may be made by any method known in the art. By way of example and not limitation, the structural member may be fabricated from a rectangular blank by removing the missing portions by any standard means such as punching, stamping, milling, or laser cutting. The curved corners, if provided, and the profile of at least first longitudinal end 40 may produced by any standard means such as cutting or stamping. Alternatively, by way of example and not limitation, the structural member may be cast or molded on a form.

Figure 8A:
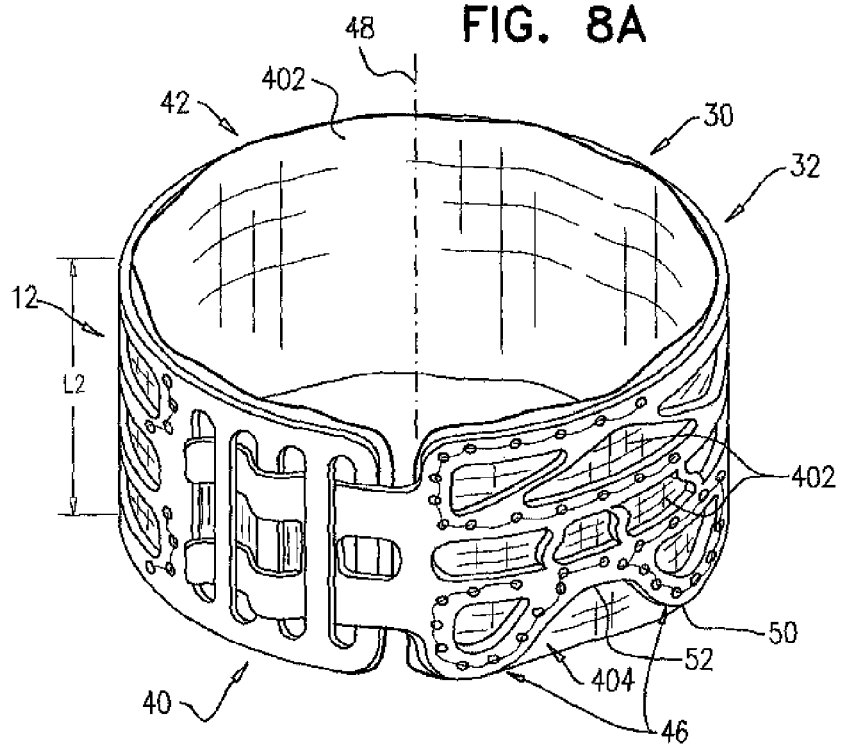
FIGS. 8A-B are schematic illustrations of two additional configurations of the extra-vascular ring of FIG. 2, in accordance with respective applications of the present invention.
Figure 8B:
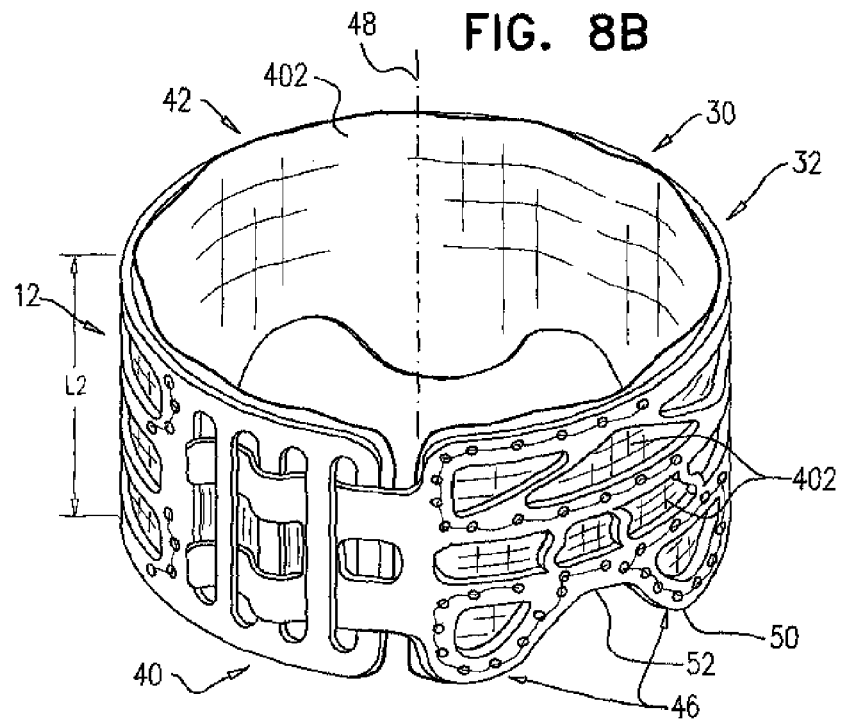

Reference is now made to FIGS. 8A-B, which are schematic illustrations of two additional configurations of extra-vascular ring 12, in accordance with respective applications of the present invention. Extra-vascular ring 12 may implement either of these configurations in combination with any of the configurations described hereinabove, including with reference to FIGS. 2, 5, 6, and 7. In these configurations, extra-vascular ring 12 further comprises a textile member 402, securely attached to and at least partially covering structural member 30 (typically an inner surface of the ring).

Textile member 402 comprises an implantable-grade, biologically-compatible fabric, and may comprise, for example, a polyester, a polyethylene (e.g., a poly-ethylene-terephthalate), a polypropylene mesh, a polymeric film material (e.g., polytetrafluoroethylene), a polymeric textile material (e.g., woven polyethylene terephthalate (PET)), natural tissue graft (e.g., saphenous vein or collagen), or a combination thereof. For some applications, textile member 402 comprises a macroporous medical textile member mention, such as described in US Patent Application Publication 2010/0292774 to Shalev, which is assigned to the assignee of the present application and is incorporated herein by reference. Alternatively or additionally, extra-vascular ring 12 comprises an external microporous layer, such as described in the '774 publication.

For some applications, as shown in FIG. 8A, textile member 402 is shaped so as to define portions 404 that extend between adjacent curved peaks 50. Portions 404 are configured to provide sufficient slack to allow the excess circumference to expand into the spaces provided by the corrugated profile, as described hereinabove with reference to FIGS. 3A-B. For other applications, as shown in FIG. 8B, textile member 402 does not define portions 404, but rather is shaped so as to provide open areas between adjacent curved peaks 50. For example, the edge of the textile member may coincide with and have the same shape as the corrugated profile; in this configuration, a first longitudinal end of extra-vascular ring 12 coincides with first longitudinal end 40 of structural member 30, such that the first longitudinal end of extra-vascular ring 12 has the profile that defines the series of curved portions and has no singularities or discontinuities, e.g., the corrugated profile. Alternatively, the textile member may partially extend between adjacent curved peaks 50 (configuration not shown).

Reference is now made to FIGS. 9A-D, which are schematic illustrations of a delivery system 410 and method for delivering extra-vascular ring 12 around aorta 20, in accordance with an application of the present invention. Delivery system 10 may be used for delivering extra-vascular ring 12 around aorta 20 (as shown) or other tissue, such as an organ, e.g., as a tubular organ, e.g., another blood vessel or a nerve. Delivery system 410 comprises a catheter 430, which comprises an outer pull-back shaft 432 having generally rectangular cross sections. The outer pull-back shaft serves as a delivery shaft. Extra-vascular ring 12 is initially removably disposed within outer pull-back shaft 432, with the extra-vascular ring in a deformed generally planar state, as shown in FIG. 5, 6, or 7. Alternatively, extra-vascular ring 12 is in a rolled state when initially disposed within the outer pull-back shaft (configuration not shown), in which case outer pull-back shaft 432 typically does not have generally rectangular cross sections.

During a first stage of an implantation procedure performed using delivery system 410, a surgeon creates a working channel, typically laparoscopically or hand-assisted laparoscopically, to an external surface of a portion of a target organ, such as aorta 20, e.g., neck 16 of an aneurysmal aorta, such as a sub-renal neck 16 immediately inferior (e.g., caudally adjacent) to the renal arteries, as shown in FIGS. 9A-D, or a supra-renal neck, an ascending aortic neck, or a neck adjacent the right subclavian artery (locations not shown). The surgeon advances a distal portion of delivery system 410 to the target organ, such as aorta 20, as shown in FIG. 9A. Typically, the surgeon advances a distal end 436 of outer pull-back shaft 432 slightly beyond the far side of the aorta, such that that outer pull-back shaft 432 is tangential to the aorta, as shown in FIG. 9A.

As shown in FIG. 9B, the surgeon subsequently proximally withdraws pull-back shaft 432, while simultaneously preventing proximal movement of extra-vascular ring 12 using a stopper shaft. The stopper shaft is not shown in FIG. 9B; the stopper shaft may be implemented using techniques described in PCT Application PCT/IL2012/000083, filed Feb. 16, 2012, entitled, "Vascular bands and delivery systems therefor," which published as PCT Publication WO 2012/111006, is assigned to the assignee of the present application and is incorporated herein by reference, with reference to FIGS. 3A-14C thereof. Techniques described herein may also be implemented in combination with other techniques described in the '083 application, and/or with techniques described in U.S Patent Application Publication 2010/0292774, which is assigned to the assignee of the present application and is incorporated herein by reference.

Withdrawal of the pull-back shaft deploys extra-vascular ring 12 from distal end 436 of pull-back shaft 432. The extra-vascular ring is configured to assume a curved shape upon deployment, and thus wraps around the organ, e.g., the aorta, as the ring is deployed, as shown in FIG. 9B. For some applications, the ring is self-curling, and, to this end, typically comprises a shape memory material, such as a super-elastic metal, e.g., Nitinol, which is heat-set to assume the curled configuration, e.g., a circularly-, helically-, or spirally-bent configuration. For some applications, structural member 30 is configured to automatically transition from the deformed state to a relaxed state as the structural member is deployed from pull-back shaft 432.

FIG. 9C shows pull-back shaft 432 and extra-vascular ring 12 after the ring has been fully deployed from the shaft. As can be seen, the ring encircles at least a portion of the organ, e.g., the aorta, such as only a portion of or the entire organ. As can also be seen, the surgeon has oriented ring 12 such that first longitudinal end 40 is inferior to second longitudinal end 42, with first longitudinal end 40 positioned at an inferior end of neck 16 and second longitudinal end 42 positioned at a superior end of neck 16.

When deployed around neck 16 of an aneurysmal aorta, extra-vascular ring 12 creates a landing zone for endovascular stent-graft 14 (which optionally is bifurcated, as shown). As shown in FIG. 9D, endovascular stent-graft 40 is deployed in the aorta, spanning an aneurysm 22 thereof. A distal portion of the stent-graft is positioned against the internal wall of the aorta at the landing zone. The landing zone provided by extra-vascular ring 12 helps create a non-leaking seal between the stent-graft and the wall of the aorta. Extra-vascular ring 12 thus helps secure aneurismal neck 16 from widening and/or leaking. Optionally, intravascular ring 12 is secured or otherwise attached (optionally, reversibly) to intravascular stent-graft 14, in order to prevent dislocation of the ring and the intravascular stent-graft along the aorta.

Alternatively, for some applications, endovascular stent-graft 14 is implanted first, and subsequently extra-vascular ring 12 is placed around the aorta.

For some applications, after placement around the aorta, elongate hollow shape 32 of extra-vascular ring 12 subtends an arc of less than 360 degrees, i.e., does not fully surround the aorta. Alternatively, the elongate hollow shape is circumferentially complete upon placement around the aorta.

For some applications, a method for treating an aortic aneurysm comprises (a) identifying a subject having an aneurysm of the abdominal aorta; (b) providing extra-vascular ring 12 in any of the configurations described herein; and (c) positioning the ring around the aorta, inferior to the renal arteries, optionally laparoscopically. Typically, the ring is compressed to a deformed state during delivery and positioning. The method may further comprise providing intravascular stent-graft 14, and placing the intravascular stent-graft into the aneurysmatic aorta in the subject, optionally laparoscopically. For some applications, identifying the subject having the aneurysm of the abdominal aorta comprises identifying the subject having the aneurysm of the abdominal aorta that is likely to rupture. For some applications, identifying the subject having the aneurysm of the abdominal aorta that is likely to rupture defining an aneurysm of the abdominal aorta that is likely to rupture as an aneurysm that is located within about 2 cm of a renal artery, and determining that the abdominal aneurysm is within about 2 cm of a renal artery of the subject.

For some applications, after placing extra-vascular ring 12 around the aorta, the ring is closed using a closure assembly that comprises one or more fastening elements, such as tab 200 and extension 210, described hereinabove with reference to FIG. 6, or tab 300 and extension 310, described hereinabove with reference to FIG. 7. Alternatively, the ring may be closed using other fastening techniques. By way of example and not limitation, the ring may be closed using fastening elements selected from the group consisting of: threads, screws, hooks, zips, fasteners, clips, flaps, claspers, springs, claspers, staplers, grips, zippers, hooks and corresponding eyes, hook and loop reclosable fastener squares, hook and loop reclosable fastener strips, hook and loop reclosable fastener dots, hook-and-loop fasteners such as Velcro-type fasteners, straps, holes and string, sutures, wires, cables, tabs, poppers, nails, buttons and corresponding button holes, press button brackets, glues, adhesives, or any combination thereof.

As used in the present application, including in the claims, "tubular" means having the form of an elongate hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

As used herein, terms referring to polygonal figures (e.g., triangles or rectangles) are to be understood as including substantially polygonal figures with rounded corners and/or substantially polygonal figures bounded by curves other than straight lines. As a non-limiting example, the term "triangle" includes shapes such as those of the triangular portions 160, described hereinabove with reference to FIG. 5, which have rounded corners.

Furthermore, descriptions of geometric shapes in terms of their ideal geometry are not intended to limit the invention to the ideal geometry, but may include deviations from the ideal geometry that are produced when the invention is used in practice. As a non-limiting example, rolling a rectangle so that two opposite sides meet will form a cylinder. In the description herein, the rolling of a substantially rectangular piece into a substantially cylindrical ring may be treated as if the piece and the ring are ideal geometric figures. The scope of the invention however includes cases where in practice the substantially cylindrical ring thus formed is oblique, such as because of imperfections in manufacturing or errors by the surgeon. Such terms as, for example, "longitudinal axis" and "transverse" are intended only as a means of providing a description of the invention that is sufficiently detailed so as to be understood by one of ordinary skill in the art. With reference to geometrical figures, the term "substantially" is taken to mean that the object in question would be recognized by one of ordinary skill in the art as being intended to have the constraints implied by the term modified by the word "substantially." Unless explicitly stated to the contrary, descriptions of geometrical figures are not intended to imply that the figures thus created are within any specific maximum deviation from the ideal structure.

The scope of the present invention includes embodiments described in the following applications, which are assigned to the assignee of the present application and are incorporated herein by reference. In an embodiment, techniques and apparatus described in one or more of the following patent applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

PCT Application PCT/IL2007/001312, filed Oct. 29, 2007, which published as PCT Publication WO/2008/053469 to Shalev, and U.S. application Ser. No. 12/447,684 in the national stage thereof, which published as US Patent Application Publication 2010/0070019 to Shalev U.S. Provisional Application 60/991,726, filed Dec. 2, 2007

PCT Application PCT/IL2008/001621, filed Dec. 15, 2008, which published as PCT Publication WO 2009/078010, and U.S. application Ser. No. 12/808,037 in the national stage thereof, which published as US Patent Application Publication 2010/0292774

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208, and U.S application Ser. No. 13/380,278 in the national stage thereof, which issued as U.S Pat. No. 8,870,938

PCT Application PCT/IL2010/000549, filed Jul. 8, 2010, which published as PCT Publication WO 2011/004374

PCT Application PCT/IL2010/000564, filed Jul. 14, 2010, which published as PCT Publication WO 2011/007354, and U.S application Ser. No. 13/384,075 in the national stage thereof, which published as U.S Patent Application Publication 2012/0179236

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2010/001087, filed Dec. 27, 2010, which published as PCT Publication WO 2011/080738

PCT Application PCT/IL2011/000135, filed Feb. 8, 2011, which published as PCT Publication WO 2011/095979

PCT Application PCT/IL2011/000801, filed Oct. 10, 2011, which published as PCT Publication WO 2012/049679

U.S. application Ser. No. 13/031,871, filed Feb. 22, 2011, which published as US Patent Application Publication 2011/0208289

PCT Application PCT/IL2012/000083, filed Feb. 16, 2012, which published as PCT Publication WO 2012/111006.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for attachment to an aorta of a patient, the apparatus comprising:
   an extra-vascular ring, which comprises a structural member, which is configured to assume, when in a relaxed state, an elongate hollow shape, which (a) has first and second longitudinal ends that are curved at least partially around a longitudinal axis defined by the elongate hollow shape, and (b) is suitable for placement at least partially around the aorta so as to provide a generally cylindrical landing zone; and
   an endovascular stent-graft, which is suitable for endovascular placement inside the aorta such that a portion of the endovascular stent-graft is positioned against an internal wall of the aorta at the landing zone provided by the structural member,
   wherein, if the structural member is unrolled to a planar shape, one side of the planar shape is defined by the first longitudinal end of the structural member, and at least the first longitudinal end has a profile that defines a series of curved portions and has no singularities or discontinuities, which profile extends along at least 50% of the first longitudinal end, wherein the profile is a corrugated profile that defines a series of smooth undulations that are shaped so as to define alternating curved peaks and curved valleys, which curved peaks extend in a direction away from the second longitudinal end and have a radius of curvature equal to at least 3% of a length of the first longitudinal end,
   wherein the length of the first longitudinal end is measured around the longitudinal axis when the structural member is in the relaxed state, and
   wherein the structural member comprises a plurality of stent struts, and wherein, if the structural member is unrolled to the planar shape, at least one of the stent struts extends completely alongside at least two of the undulations, such that the strut substantially prevents longitudinal stretching of the at least two of the undulations.

2. The apparatus according to claim 1, wherein the corrugated profile has a substantially sinusoidal form.

3. The apparatus according to claim 1, wherein the at least one of the stent struts geometrically encompasses at least one straight line segment that is parallel to the one side and extends completely alongside the at least two of the undulations, when the structural member has the planar shape.

4. The apparatus according to claim 1, wherein the at least one of the stent struts is straight when the structural member has the planar shape.

5. The apparatus according to claim 1, wherein, when the structural member has the planar shape, the at least one stent strut has a length, measured in a direction parallel to the one side, equal to at least 90% of a length of the one side.

6. The apparatus according to claim 1, wherein the profile defines the series of curves interspersed with one or more straight portions.

7. The apparatus according to claim 1,
wherein, if the structural member is unrolled to the planar shape, the length of the first longitudinal end is equal to between 30 and 120 mm, and
wherein the elongate hollow shape has a longitudinal length, measured parallel to the longitudinal axis of the elongate hollow shape, that equals between 10 and 40 mm.

8. The apparatus according to claim 1,
wherein the structural member, when having the elongate hollow shape, is shaped so as to define a gap that extends longitudinally along an entire longitudinal length of the elongate hollow shape from the first longitudinal end to the second longitudinal end, and
wherein the structural member is shaped so as to define (a) a first extension, which first extension defines at least one slot, and (b) a second extension, which is shaped so as to define a tab adapted to fit into the at least one slot, such that inserting the tab into the slot closes the gap.

9. The apparatus according to claim 1,
wherein the structural member, when having the elongate hollow shape, is shaped so as to define a gap that extends longitudinally along an entire longitudinal length of the elongate hollow shape from the first longitudinal end to the second longitudinal end, and
wherein the extra-vascular ring further comprises one or more fastening elements for closing the gap.

10. The apparatus according to claim 1, further comprising a hollow, generally tubular delivery shaft, in which the extra-vascular ring is removably disposed with the structural member in a deformed state.

11. The apparatus according to claim 1, wherein the structural member comprises a shape memory material, which is heat-set to assume the elongate hollow shape.

12. A method comprising:
providing an extra-vascular ring, which includes a structural member, which is configured to assume, when in a relaxed state, an elongate hollow shape, which has first and second longitudinal ends that are curved at least partially around a longitudinal axis defined by the elongate hollow shape, wherein, if the structural member is unrolled to a planar shape, one side of the planar shape is defined by the first longitudinal end of the structural member, and at least the first longitudinal end has a profile that defines a series of curved portions and has no singularities or discontinuities, which profile extends along at least 50% of the first longitudinal end; wherein the profile is a corrugated profile that defines a series of smooth undulations that are shaped so as to define alternating curved peaks and curved valleys, which curved peaks extend in a direction away from the second longitudinal end and have a radius of curvature equal to at least 3% of a length of the first longitudinal end; wherein the length of the first longitudinal end is measured around the longitudinal axis when the structural member is in the relaxed state; and wherein the structural member comprises a plurality of stent struts; and wherein, if the structural member is unrolled to the planar shape, at least one of the stent struts extends completely alongside at least two of the undulations, such that the strut substantially prevents longitudinal stretching of the at least two of the undulations;
placing the extra-vascular ring at least partially around a neck of an aneurysmal aorta of a patient so as to provide a generally cylindrical landing zone, such that the profile homogenously distributes strain on aortic tissue at the first longitudinal end of the structural member; and
placing an endovascular stent-graft inside the aorta such that a portion of the endovascular stent-graft is positioned against an internal wall of the neck at the landing zone provided by the structural member.

13. The method according to claim 12,
wherein placing the extra-vascular ring comprises advancing, to an external surface of the aorta, a hollow, generally tubular delivery shaft, in which the extra-vascular ring is removably disposed with the structural member in a deformed state, and
wherein advancing the delivery shaft comprises advancing the delivery shaft through a laparoscopic working channel to an abdominal location adjacent to renal arteries of the aorta, and laparoscopically placing the extra-vascular stent around the neck of the abdominal aorta in a vicinity of the renal arteries.

14. The method according to claim 12, wherein providing the extra-vascular ring comprises providing the extra-vascular ring in which the corrugated profile has a substantially sinusoidal form.

15. The method according to claim 12, wherein providing the extra-vascular ring comprises providing the extra-vascular ring in which the at least one of the stent struts geometrically encompasses at least one straight line segment that is parallel to the one side and extends completely alongside the at least two of the undulations, when the structural member has the planar shape.

16. The method according to claim 12, wherein providing the extra-vascular ring comprises providing the extra-vascular ring in which the at least one of the stent struts is straight when the structural member has the planar shape.

17. The method according to claim 12, wherein providing the extra-vascular ring comprises providing the extra-vascular ring in which, when the structural member has the planar shape, the at least one stent strut has a length, measured in a direction parallel to the one side, equal to at least 90% of a length of the one side.

18. The method according to claim 12, wherein providing the extra-vascular ring comprises providing the extra-vascular ring in which the profile defines the series of curved portions interspersed with one or more straight portions.

19. The method according to claim 12, wherein placing the extra-vascular ring comprises advancing, to an external surface of the aorta, a hollow, generally tubular delivery shaft, in which the extra-vascular ring is removably disposed with the structural member in a deformed state.

20. The method according to claim 12, wherein placing the extra-vascular ring comprises identifying the patient as suffering from an aneurysm of an abdominal aorta, and treating the aortic aneurysm by placing the extra-vascular ring at least partially around the neck of the abdominal aorta.

21. The method according to claim 12, wherein providing the extra-vascular ring comprises providing the extra-vascular ring in which the structural member comprises a shape memory material, which is heat-set to assume the elongate hollow shape.

* * * * *